US005467911A

United States Patent [19]

Tsuruta et al.

[11] Patent Number: 5,467,911

[45] Date of Patent: Nov. 21, 1995

[54] SURGICAL DEVICE FOR STAPLING AND FASTENING BODY TISSUES

[75] Inventors: Minoru Tsuruta; Toshihiko Suzuta; Akio Nakada; Seiji Kuramoto; Hiroki Hibino; Shiro Bito; Akito Mukaizawa, all of Tokyo, Japan

[73] Assignee: Olympus Optical Co., Ltd., Tokyo, Japan

[21] Appl. No.: 231,241

[22] Filed: Apr. 22, 1994

[30] Foreign Application Priority Data

| | | | |
|---|---|---|---|
| Apr. 27, 1993 | [JP] | Japan | 5-101163 |
| Apr. 27, 1993 | [JP] | Japan | 5-101169 |
| Apr. 27, 1993 | [JP] | Japan | 5-101170 |
| Jun. 8, 1993 | [JP] | Japan | 5-137422 |

[51] Int. Cl.[6] .......... A61B 17/068

[52] U.S. Cl. .......... 227/175; 227/19; 227/179

[58] Field of Search .......... 227/175, 176, 227/178, 179, 19

[56] References Cited

U.S. PATENT DOCUMENTS

| | | | |
|---|---|---|---|
| 4,319,576 | 3/1982 | Rothfuss . | |
| 4,944,443 | 7/1990 | Oddsen et al. . | |
| 5,040,715 | 8/1991 | Green et al. . | |
| 5,084,057 | 1/1992 | Green et al. . | |
| 5,333,773 | 8/1994 | Main et al. | 227/19 |

FOREIGN PATENT DOCUMENTS

| | | |
|---|---|---|
| 0552050 | 7/1993 | European Pat. Off. . |

*Primary Examiner*—Scott A. Smith

*Attorney, Agent, or Firm*—Frishauf, Holtz, Goodman, Langer & Chick

[57] ABSTRACT

Disclosed herein is a surgical device for applying surgical fasteners to body tissues in order to fasten the body tissues together. The device comprises an operation section having a housing having an inner space completely sealed from the outside, drive elements electrically driven and arranged in the inner space of the operation section, an insertion section including a housing which has a first end portion containing the fasteners and having an opening through which the fasteners are to be applied, and a second end portion removably coupled to the housing of the operation section, fastener-applying elements located in the housing of the insertion section, for applying the fasteners from the opening to body tissues, and force-transmitting elements for transmitting drive force from the drive elements to the fastener-applying elements.

20 Claims, 22 Drawing Sheets

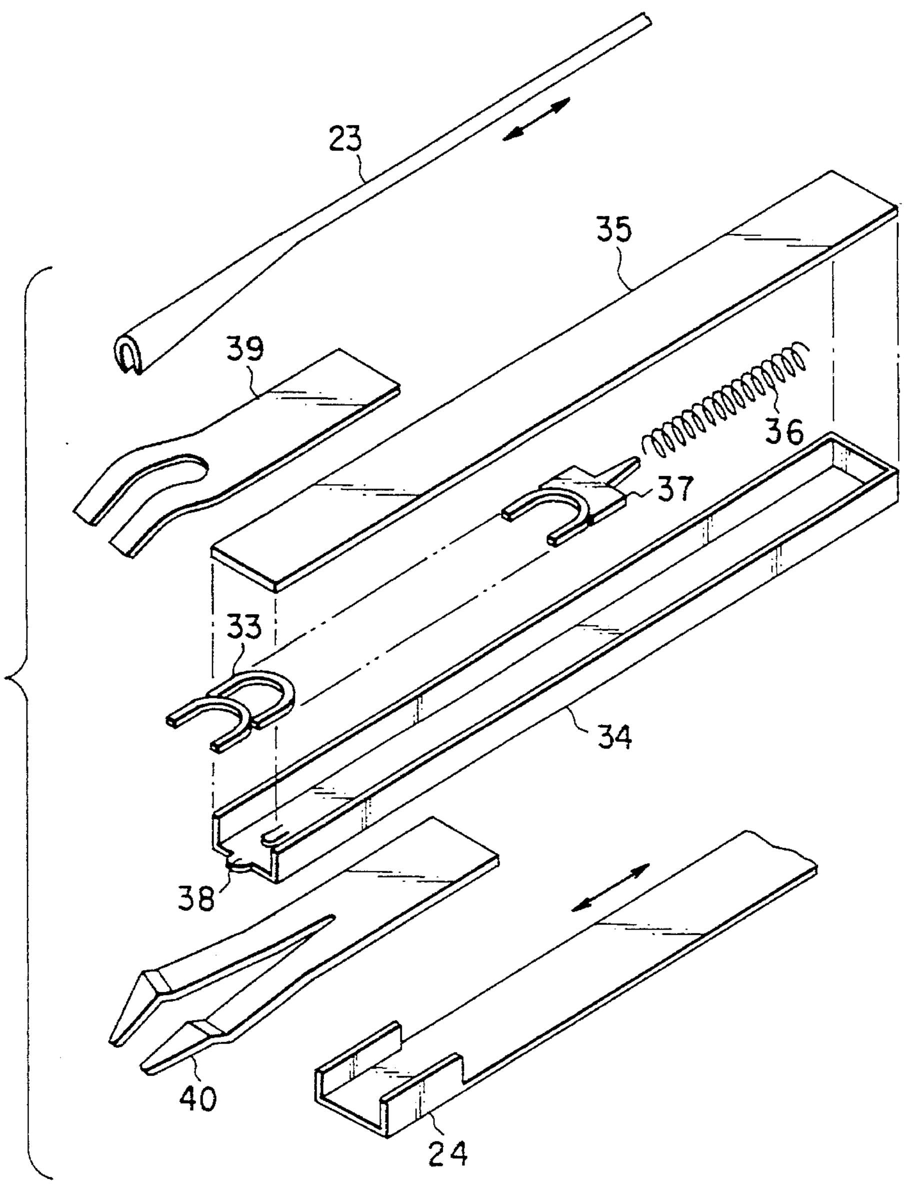
F I G. 4
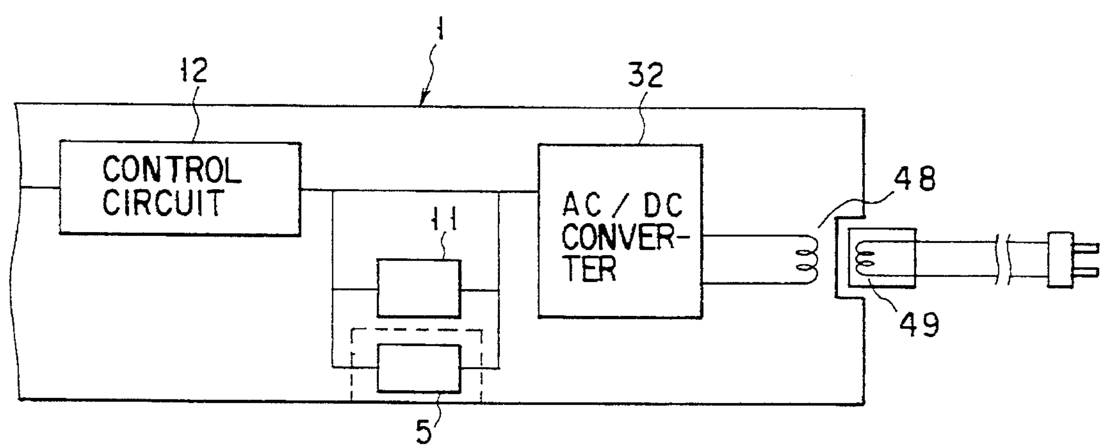
F I G. 5

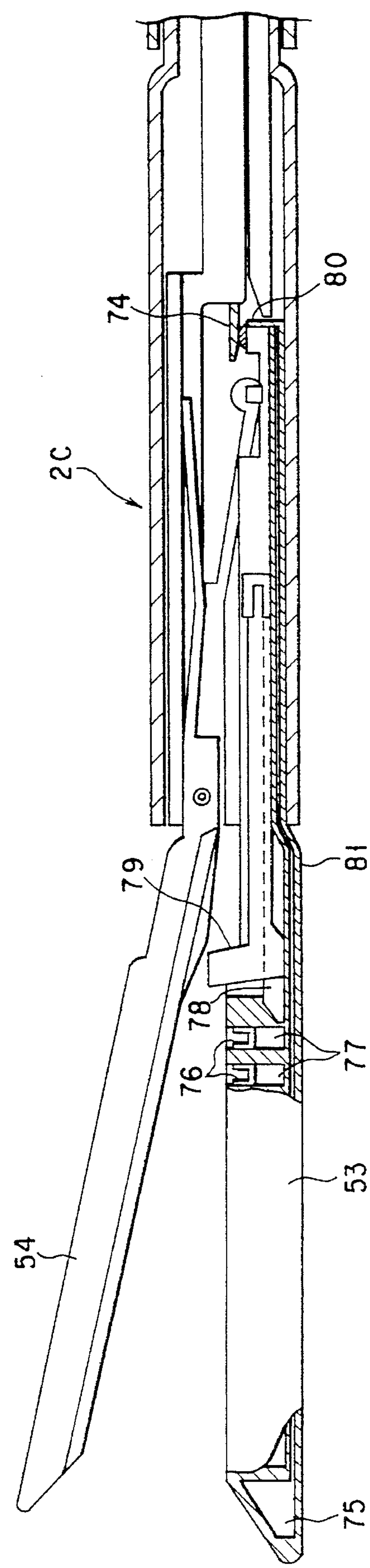
F I G. 11

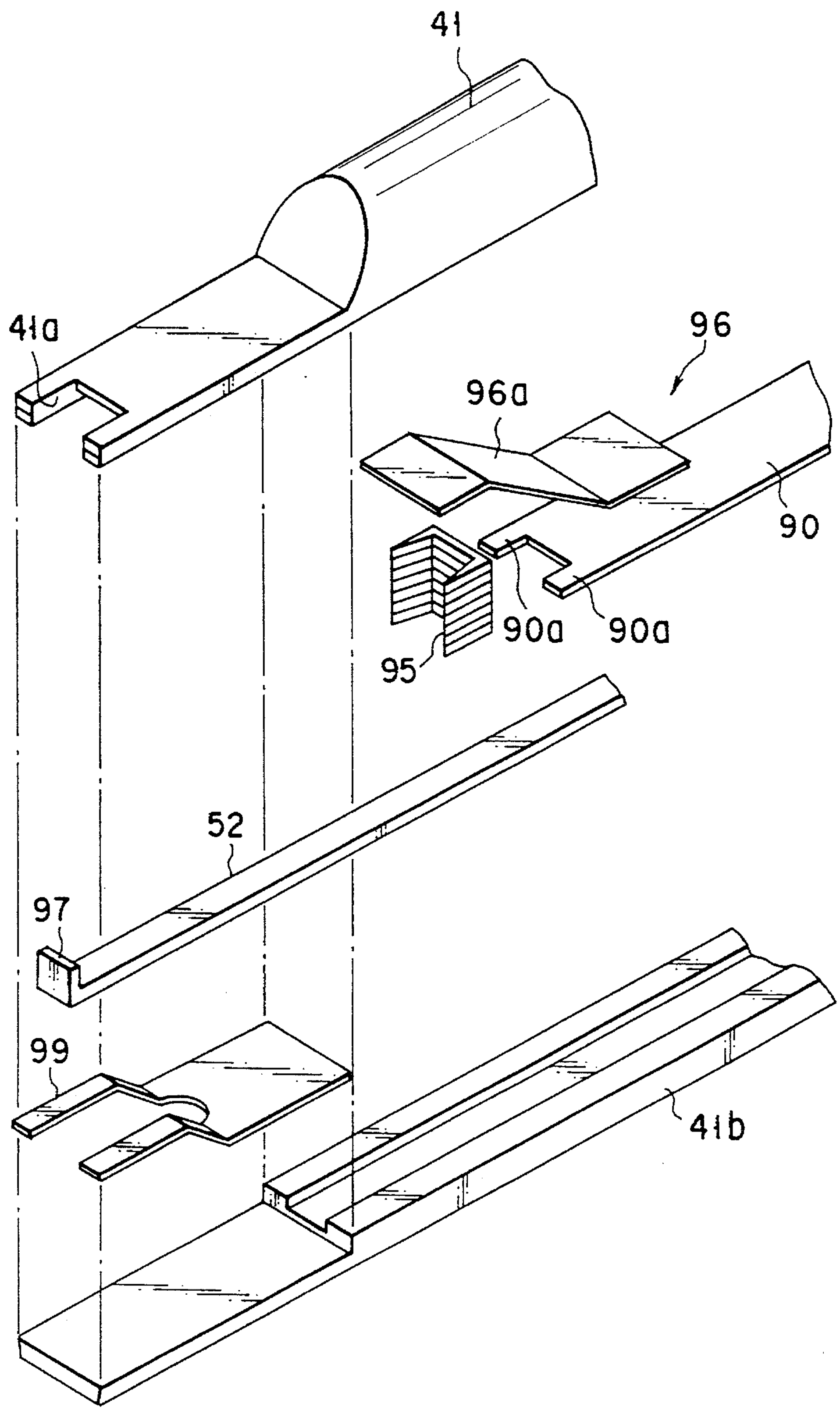
F I G. 14

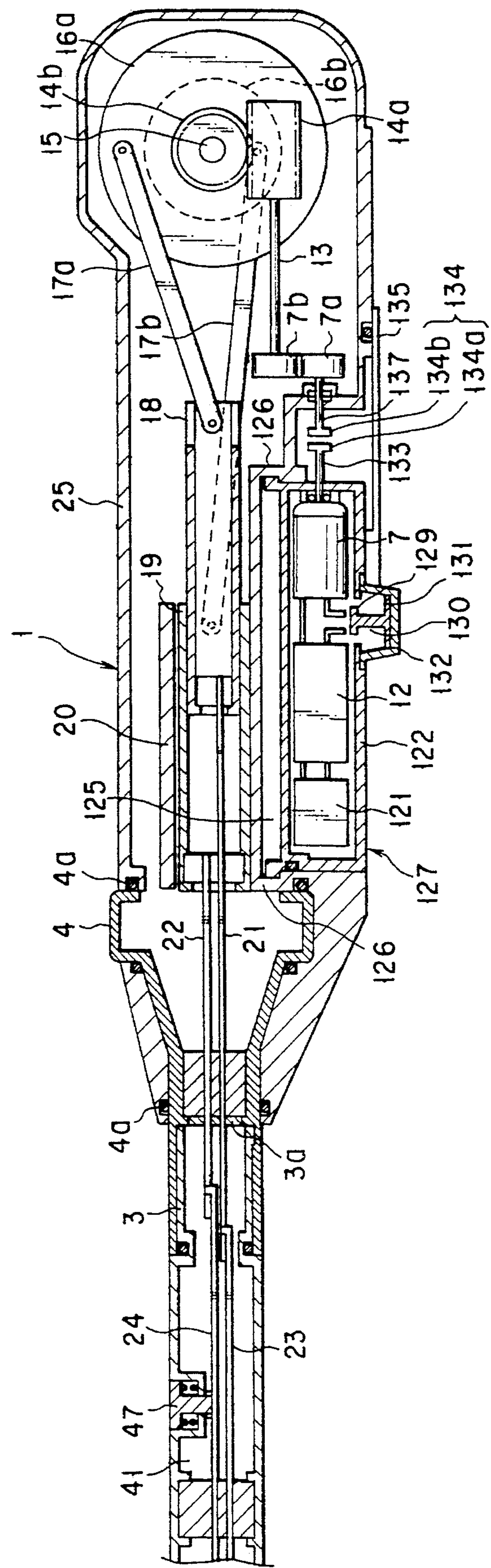
F I G. 22

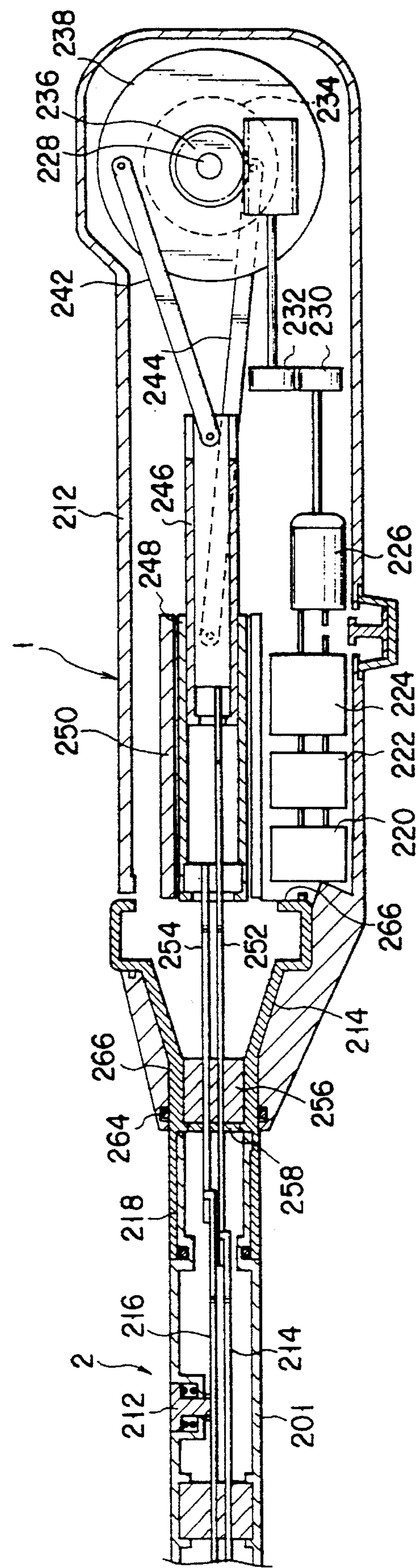
F I G. 24

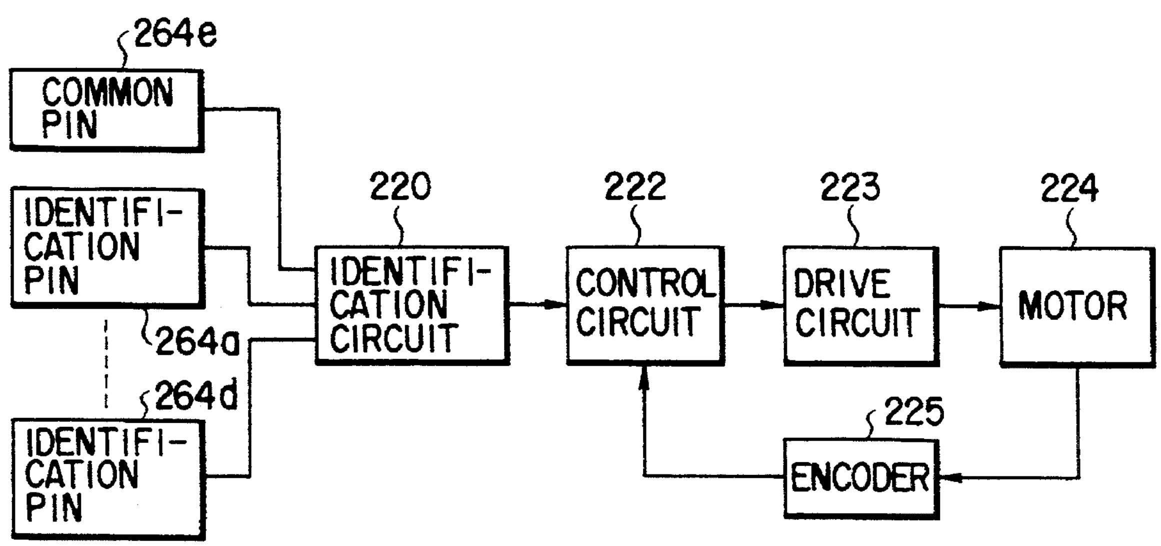
F I G. 25

SURGICAL DEVICE FOR STAPLING AND FASTENING BODY TISSUES

BACKGROUND OF THE INVENTION

1. Field of the Invention

The present invention relates to a surgical device for applying fasteners to body tissues in order to suture and/or ligete the body tissues together.

2. Description of the Related Art

There is a case that the gallbladder needs to be extracted in order to prevent recurrence of gallstones. To extract the gallbladder, the cystic duct must be cut. Since the gallbladder arteries and veins extend through the cystic duct, the cystic duct must be sutured and/or ligated at a portion at the same time it is cut at that portion.

A tissue-fastening device is used to suture and/or ligate and a portion of the cystic duct in removing gallstones. The device is inserted into the body cavity through an incision made in the abdominal wall of the patient. The device is manipulated to apply staples, for example, to that portion of the cystic duct. A device of this type is disclosed in, for example, U.S. Pat. No. 5,084,057 and Jpn. Pat. Appln. KOKAI Publication No. 3-12126.

The device disclosed in U.S. Pat. No. 5,084,057 is designed to apply clips to tissues located in a body, to thereby fasten the tissues together. The device disclosed in Jpn. Pat. Appln. KOKAI Publication No. 3-12126 is of the type which is transcutaneously inserted into a body cavity to suture and ligate the tissues in the cavity. This device comprises an operation section; an insertion section connected to the operation section; a stapler attached to the distal end of the insertion section, including an anvil and a cartridge holding staples, capable of opening and closing; a firing lever for ejecting the staples from the cartridge; and a stapler-actuating lever for opening and closing the stapler.

While the tissue-fastening device is being used to staple and fasten the body tissues, the operation section, as well as the the insertion section, is contaminated with blood and other body fluids. The tissue-fastening device must therefore be washed and sterilized before it is used again. The device may be sterilized by various methods, such as gas sterilization, liquid-medicine immersion, or high-pressure, high-temperature sterilization in an autoclave. The autoclave sterilization is regarded as the best for environmental sanitation, since it achieves sterilizing with high efficiency and it does not use toxic gases or toxic liquid medicine.

The operation section of the conventional tissue-fastening device is not made liquid-tight. Water an liquid medicine may enter the device, damaging the internal components of the device. An electrically driven device has been developed, in which the fastening mechanism is driven by an electric motor provided in the operation section. The motor is driven by the power supplied from the dry cell or the battery contained in the device. When the device is sterilized in an autoclave, at a high temperature and a high pressure, the electrolytic solution will leak from the dry cell or battery. Furthermore, as well known, a dry cell and a battery are easily damaged by water or liquid medicine. Therefore, only gas sterilization may be applied to a tissue-fastening device containing a dry cell or a battery.

Certainly, the device containing a dry cell or a battery may have means for protecting the cell or battery from high temperatures and high pressures, so that the device may be sterilized in an autoclave. However, the use of such protective means will inevitably render the device complex, large and expensive.

Even if provided with such protective means, a device containing a dry cell or a battery causes a problem. Once used up, the cell or battery must be removed from the device, and a new one must be loaded into the device. If the cell or battery has not been sterilized, a person who removes it inevitably has his or her hands contaminated with dirt on the cell or battery.

The dry cell or the battery may be removed from the tissue-fastening device before the device is subjected to autoclave sterilization, and may be loaded back into the device after the device has been sterilized in the autoclave. However, it would be very cumbersome and time-consuming to open the cover of the cell or battery case and remove the cell or battery from the case. It would equally troublesome to load the cell or battery back into the case and close the cover of the case.

SUMMARY OF THE INVENTION

In view of the foregoing, the object of the present invention is to provide a surgical device for fastening body tissues, whose operation section can be easily washed and sterilized, and which is easy to operate.

According to the present invention, there is provided a surgical device for fastening body tissues, comprising: an operation section having a housing having an inner space completely sealed from the outside; drive means electrically driven and arranged in the inner space of the operation section; an insertion section including a housing which has a first end portion containing the fasteners and having an opening through which the fasteners are to be applied, and a second end portion removably coupled to the housing of the operation section; fastener-applying means located in the housing of the insertion section, for applying the fasteners from the opening to body tissues; and force-transmitting means for transmitting drive force from the drive means to the fastener-applying means.

Since the electric drive means is located in the sealed housing of the operation section, it is possible to sterilize the operation section only, after detaching the used insertion section from the operation section. After sterilized, the operation section can be used again, with a new insertion section coupled to it. The operation section can be sterilized in any method considered appropriate. Hence, the operation section can be maintained in sanitary condition. Furthermore, the operation section is easy to operate, and is so designed to make it easy to connect the insertion section to it and disconnect the same from it.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is an exploded view showing the internal structure of the distal end portion of the device shown in FIG. 1;

FIG. 5 is a circuit diagram showing a section of a modification of the device, which can be supplied with electric power from an external power supply;

FIG. 11 is a longitudinal sectional view of the insertion section of the tissue-fastening device shown in FIG. 10;

FIG. 14 is an exploded view illustrating the distal end portion of the insertion section of the device shown in FIG. 13;

FIG. 22 is a longitudinal sectional view of a tissue-fastening device according to a ninth embodiment of the invention, which has a detachable electric unit;

FIG. 24 is a sectional view showing the operation section of another embodiment of the invention and also a part of the insertion section thereof; and FIG. 25 is a block diagram of an electric drive unit incorporated in the operation section shown in FIG. 24.

DETAILED DESCRIPTION OF THE PREFERRED EMBODIMENTS

Figure 1:
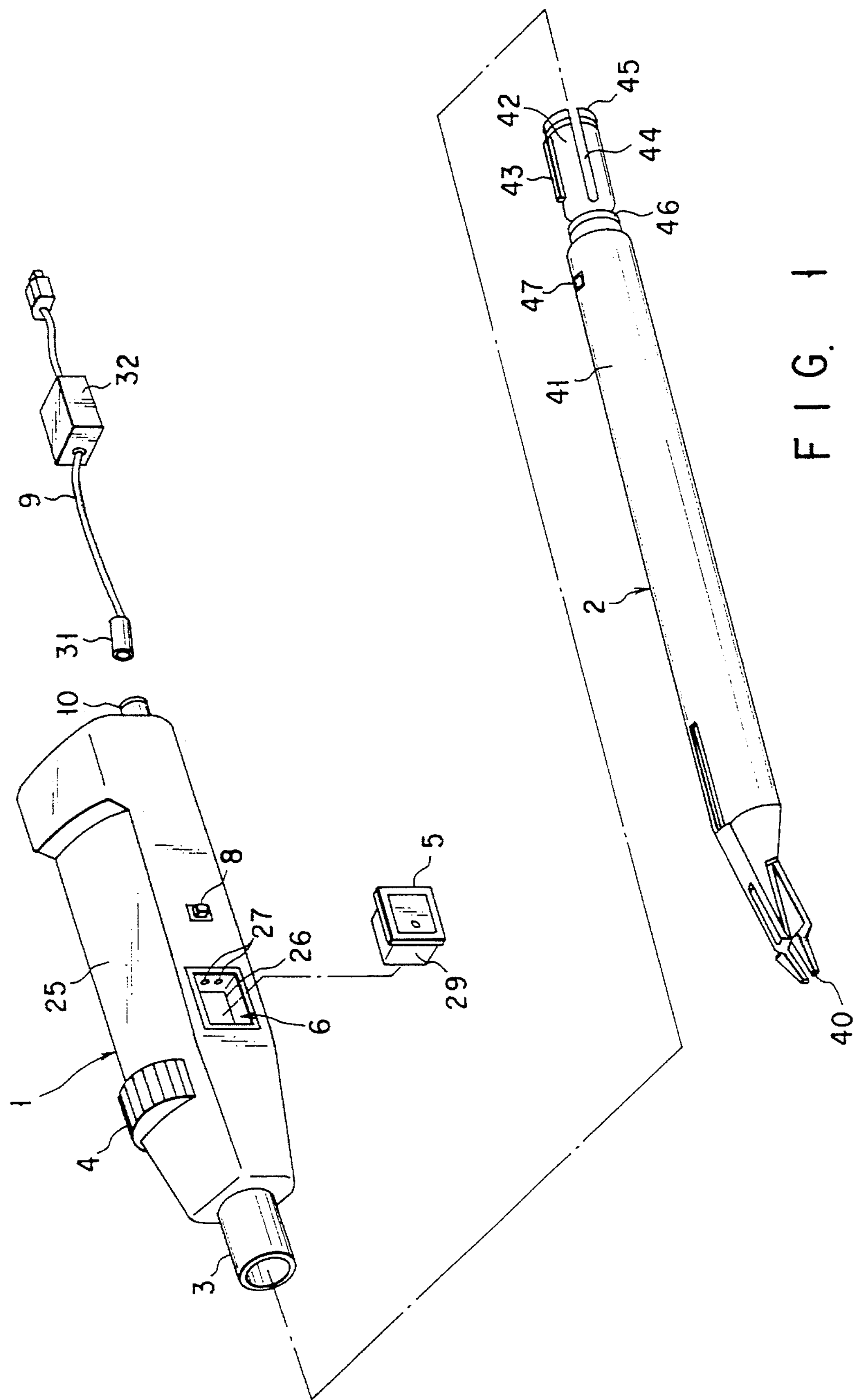
FIG. 1 is an exploded view of a tissue-fastening device according to a first embodiment of the present invention.

Embodiments of the present invention will now be described, with reference to the accompanying drawings. In the drawings, the components of each embodiment are designated at the same numerals as their counterparts of any other embodiment. In the following description, any component identical or similar to a component already described will not be described in detail.

FIGS. 1 to 4 show a first embodiment of the invention which is a device to suture and/or ligate the body tissues together. As shown in FIG. 1, the device comprises an operation section 1 and an insertion section 2. The operation section 1 comprises a first connector 3, a drive ring 4, a power supply unit 5, a second connector 6, a switch 8, a connecting cable 9, and a connector port 10. The first connector 3 is used to achieve mechanical connection with the insertion section 2. The drive ring 4 is rotated to rotate the insertion section 2 around the axis thereof. The second connector 6 and the connector port 10 are provided for achieving electrical connection with the power supply unit 5 and the connecting cable 9, respectively.

Figure 2:
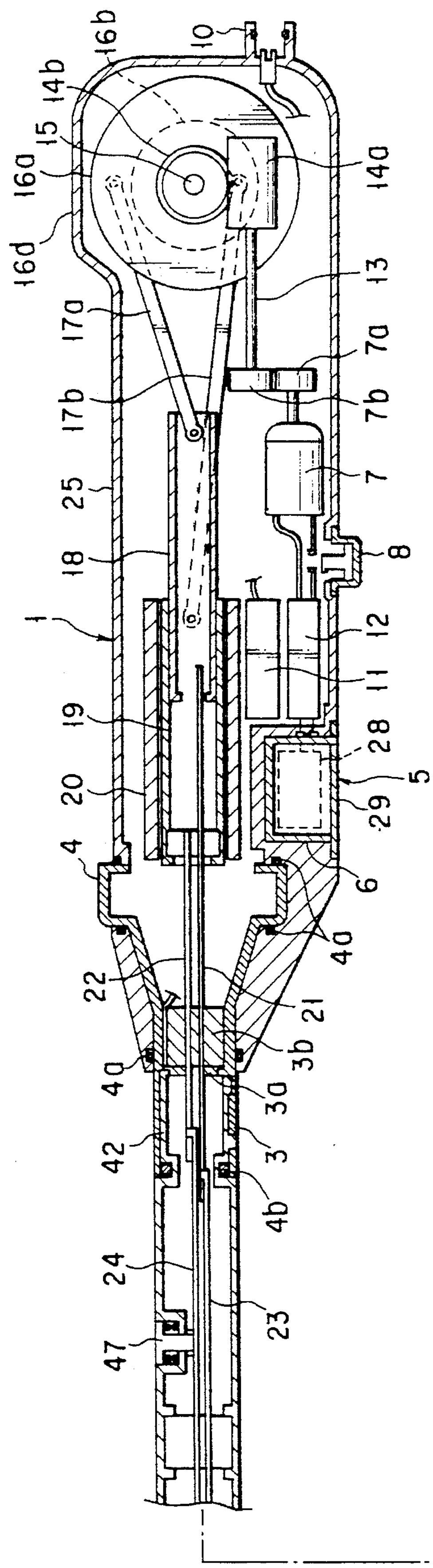
FIG. 2 is an exploded, longitudinal sectional view of the tissue-fastening device illustrated in FIG. 1.
Figure 3:
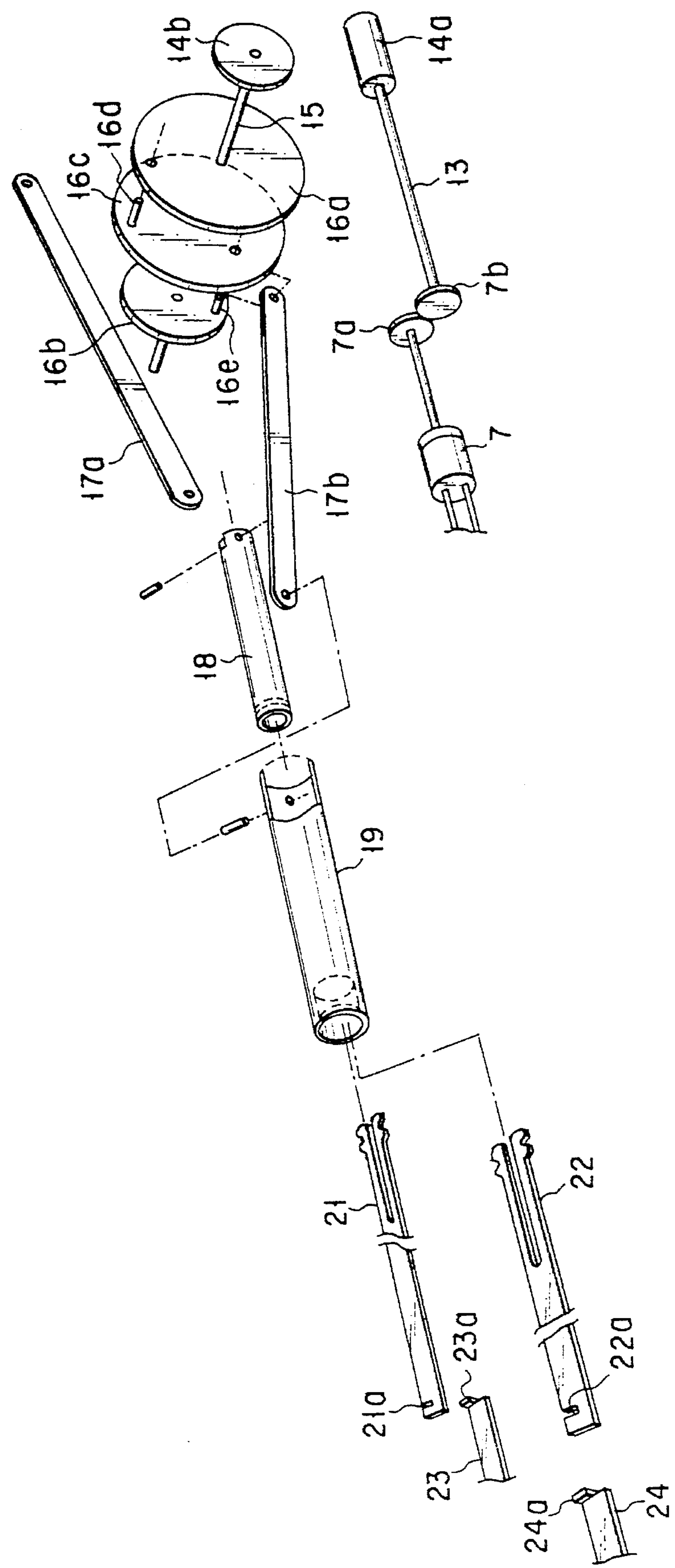
FIG. 3 is an exploded view of the electrically driven mechanism incorporated in the device shown in FIG. 1.

FIG. 2, 3 and 4 show the internal structure of the operation section 1 and that of the insertion section 2. The first connector 3 of the operation section 1 is covered by a seal member 3a, whereby the operation section 1 is made airtight as a whole. Located within the casing 25 of the operation section 1 are: an electric motor 7 such as a stepping motor, an auxiliary power supply 11, and a circuit 12 for controlling the torque, rotational speed and the like of the electric motor 7.

A first pinion 7a is mounted on the shaft of the motor 7. The first pinion 7a is in mesh with a second pinion 7b amounted on the forward end portion of a transmission shaft 13. A worm gear 14a is mounted on the rear end portion of the shaft 13. The worm gear 14a is set in engagement with a worm wheel 14b which is mounted on a drive shaft 15. Hence, the drive force of the motor 7 is transmitted to the drive shaft 15 by means of the pinions 7a and 7b, the transmission shaft 13, the worm gear 14a and the worm wheel 14b.

The drive shaft 15 is located in the proximal end portion of the operation section 1 and rotatably supported by a bearing (not shown). Mounted on the dive shaft 15 are a first pulley 16a and a second pulley 16b, the latter having a smaller diameter than the former. A disc 16c is connected to the first pulley 16a by a connecting pin 16d, so that it may rotate together with the first pulley 16a. A connecting pin 16e protrudes from the second pulley 16b.

Coupled to the connecting pin 16d is the proximal end of a first pusher link 17a. Coupled to the connecting pin 16e is the proximal end of a second pusher link 17b. The distal end of the first pusher link 17a is coupled to a first pusher tube 18, whereas the distal end of the pusher link 17b is coupled to a second pusher tube 19. The first pusher tube 18 is inserted in the second pusher tube 19 and can be moved back and forth. The second tube 19 can be moved back and forth with respect to a guide cylinder 20 which is secured to the casing 25 of the operation section 1.

A first pusher bar 21 is connected to the distal end portion of the first pusher tube 18 and can be rotated around its axis. Similarly, a second pusher bar 22 is connected to the distal end portion of the second pusher tube 18 and can be rotated around its axis. As shown in FIG. 3, the first pusher bar 21 has a notch 21a, and the second pusher bar 22 has a notch 22a. Removably put in the notch 21a of the bar 21 is a projection 23*a* formed integral with the rear end of a clip pusher 23. Removably placed in the notch 22*a* of the bar 22 is a projection 24*a* from integral with the rear end of a jaw pusher 24. The clip pusher 23 and the jaw pusher 24 extend through the insertion section 2, in parallel to each other.

The drive ring 4 provided in the casing 25 of the operation section 1 is rotatable with respect to the casing 25. The ring 4 has a sliding portion, on which there is mounted an O-ring 4*a* coated with silicone grease. The drive ring 4 consists of a front cylindrical portion and a rear funnel-shaped portion. A spacer 3*b* is arranged in the front portion of the ring 4, for positioning the pusher bars 21 and 22. The spacer 3*b* has two holes, through which the bars 21 and 22 can slide back and forth. The holes of the spacer 3*b* have such sizes and shapes that they hold the bars 21 and 22 in airtight fashion.

The second connector 6 has a rectangular recess 26 made in one side of the casing 25. Electric contacts 27 is provided on one inner surface of the recess 26. The power supply unit 5 comprises a battery 28 and an airtight case 29 containing the battery 28. Electric contacts (not shown) are mounted on one side of the case 29 and electrically connected to the control circuit 12 located in the casing 25. These contacts abut on the electric contacts 27 of the second connector 6 when the unit 5 is pushed into the recess 26. Hence, when the power supply unit 5 is set in the recess 26 of the second connector 6, it is electrically connected to the control circuit 12. No matter whether or not the unit 5 is set in the recess 26, the control circuit remains in electrical connection with the auxiliary power supply 11.

As shown in FIG. 1, a connector 31 is fastened to one end of the connecting cable 9. An AC-DC converter 32 is connected on the middle portion of the cable 9. The cable 9 can, therefore, connect the operation section 1 to an external power supply, for example a power supply for the light-source unit of an endoscope.

The insertion section 2, which is a generally tubular member, will now be described. The insertion section 2 contains a clip applicator for applying clips 33 to body tissues in a body cavity for fastening the tissues together with clips 33. As shown in FIG. 2, the clips 33 are contained in the insertion section 2. When applied to body tissues by the clip applicator, they are deformed to stitch or suture the tissues together.

More specifically, a number of clips 33 are slidably contained in a clip track 34 which is arranged in the insertion section 2. The clip track 34 is covered with a lid 35, but is opened at the front end. A pushing member 37 is inserted in the rear end portion of the clip track 34 and biased forward, thus pushing the clips 33 forward.

A claw 38 is located at the distal end of the clip track 34. An resilient member 38 is arranged above the claw 38, pressing the clips 33 downwards. Pressed so, the claw 38 prevents the clips 33 from pushed forward from the clip track 34.

A jaw 40 is provided in front of the clip track 34. The jaw 40 is forked, having two distal ends which can be elastically bent toward each other. Located below the jaw 40 is the distal end portion of the jaw pusher 24. When slid forward, the jaw pusher 24 pushes the distal ends of the jaw 40 toward each other, thereby closing the jaw 40. Located above the clip track 34 is the distal end portion of the clip pusher 23. When slid forward, the clip pusher 23 pushes the foremost clip 33 into the gap between the distal ends of the jaw 40.

The housing 41 of the insertion section 2 has a thin portion 42 at the rear, which is fitted in the first connector 3 of the operation section 1. As shown in FIG. 1, the thin portion 42 has a key 43, a slit 44, and a flange 45. An O-ring 46 is mounted on the forward end of the thin portion 42.

A release button 47 is mounted on the rear end portion of the housing 41 of the insertion insertion section 2. When the release button 47 is depressed, it pushes the clip pusher 23, releasing the projection 23*a* from the the notch 21*a* of the first pusher bar 21, and also pushes the jaw pusher 24, releasing the jaw pusher 24 from the notch 22*a* of the second pusher bar 22.

The operation of the tissue-fastening device will be explained below.

When the power supply unit 5 is fitted in the recess 26 made in one side of the casing 25 of the operation unit 1, its electric contacts (not shown) abut on the electric contacts 27 of the second connector 6. As a result, the power supply unit 5 is electrically connected to the control circuit 12 which is located in the casing 25. The control circuit 12 supplies a drive signal to the electric motor 7. The motor 7 is thereby driven. The first pinion 7*a* and the second pinion 7*b* transmit the rotation of the motor shaft to the transmission shaft 13. The worm gear 14*a* and the worm wheel 14*b* transmit the rotation of the shaft 13 to the drive shaft 15. Hence, the first pulley 16*a* and the second pulley 16*b*, both mounted on the drive shaft 15, are rotated.

At this time the first pusher link 17*a* is moved forward, causing the first pusher tube 18 to slide forward, and the second pusher link 17*b* is moved backward, causing the second pusher tube 19 to slide backward. At the distal end of the insertion section 2, the clip pusher 23 pushes the foremost clip 33 into the gap between the distal ends of the jaw 40. As the motor 7 is further driven, the first pusher tube 18 slides backward, whereas the second pusher tube 19 slides forward. As a result of this, the clip pusher 23 is pulled backward to a point behind the foremost of the clips 33 contained in the clip track 34, and the jaw pusher 24 slides forward, closing the jaw 40. The jaw 40 clamps and deforms the clip 33. As being deformed, the clip 33 can suture tissues together.

Thus, once the power supply unit 5 has been pushed into the recess 26 of the operation unit 1, the tissue-fastening device can be electrically driven to staple and fasten body tissues which are located at the distal end of the insertion section 2. Electrically driven, the device has high operability; a surgeon need not exert a large force to operate the device and will not be tired so much as otherwise. In most case, the connecting cable 9 is not used to connect the device to an external power supply, thus making no hindrance to the surgeon who is manipulating the device.

when the power of the unit 5 is used up during the use of the tissue-fastening device, the unit 5 can be replaced by a new power supply unit which has been sterilized. Electrically connected to the auxiliary power supply 11, the control circuit 12 continuously performs its function even after the used unit 5 has been removed from the recess 26.

The auxiliary power supply 11 is, for example, a nickel-cadmium battery which is rechargeable. Thus, the auxiliary power supply 11 need not be replaced by a new one at all. Since the power supply 11 is located in the operation section 1 and need not be removed therefrom, it remains protected against heat, pressure and liquid, provided it is covered with a protective member.

The power supply unit 5 may be covered with a protective member so that the device may be sterilized, with the battery 28 still contained in the airtight case 29. In this case, however, it will be impossible to replace the battery 28 with a new one during the use of the tissue-fastening device. To protect the battery 28 from high temperature, high pressure and liquid and to allow for replacement of the battery, the case 29 must be a box having an open side and a cover must be fastened by screws or the like to close the open side. It would be cumbersome and hence time-consuming to remove the cover from the box and fasten it to the box to replace the battery 28 with a new one. In view of this, it is desirable that the power supply unit 5 be a sterilized disposable one which comprises a completely sealed case and a battery contained in this case.

During the use of the tissue-fastening device, the operation section 1 and the insertion section are contaminated with blood and washing solutions. Nonetheless, the seal member 3*a* and the O-ring 46 prevents the blood and the solutions from flowing into the operation section 1. After the use of the device, the insertion section 2 and the power supply unit 5 are detached from the operation section 1, and the first connector 3 of the operation section 1 is covered with a rubber cap (not shown). This done, the operation section 1 can be readily washed and sterilized.

Once washed and sterilized in this way, the operation section 1 can be used again. This helps to reduce medical fees considerably.

FIG. 5 is a circuit diagram showing a modification of the operation section 1, which is characterized in that, instead of providing connecting terminals on the connector port 10, a primary coil 48, a secondary coil 49 and an AC/DC converter 32 are arranged between the connector cable 9*a* and the auxiliary power supply 11. Thus, electric current can be supplied to the auxiliary power supply 11 from an external power supply. If this is the case, the connector port 10 made of synthetic resin and integral with the casing 25 of the operation section 1 can be located between the primary coil 48 and the secondary coil 49. The connector port 10 can be sealed better than otherwise, and blood wetting the port 10 can be easily washed. This makes it easy to wash and sterilize the operation section 1.

Figure 6:
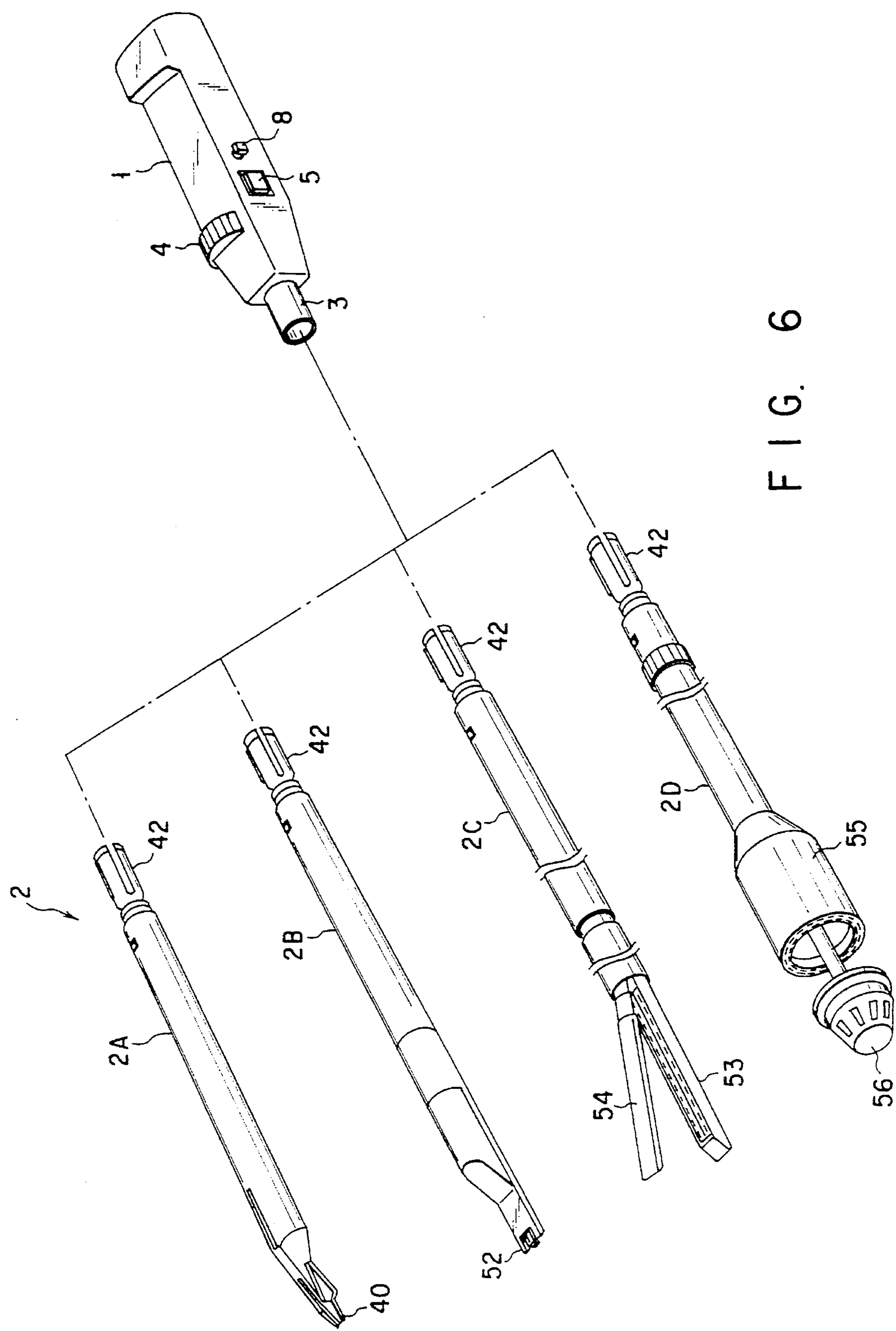
FIG. 6 is a perspective view showing the operation section of the device shown in FIG. 1, and also four different insertion sections which can be used in combination of the operation section.

FIG. 6 shows various insertion sections 2A, 2B, 2C and 2D which can be used in combination of the operation section 1. Each of these insertion sections 2 has a fastener-applying means designed for applying fasteners to body tissues in a specific manner. More specifically, the insertion section 2A is a clipper which has a jaw 40 at the distal end. The jaw 40 is of the same type as used in the first embodiment. The insertion section 2B is a stapler which has an anvil 52 at the distal end. The insertion section 2C is a linear cutter which has a cartridge 53 and an anvil 54 at the distal end. The insertion section 2D is a circular stapler which has a staple applicator 55 and an anvil 56 at the distal end.

The insertion sections 2A, 2B, 2C and 2D have a thin proximal end portion 42 each. The proximal end portions 42 of the sections 2A to 2D are of the same structure, and each is removably coupled to the first connector 3 of the operation section 1. Therefore, any one of the insertion sections 2A to 2D can be selected and connected to the operation section 1, in accordance with the body tissues to be fastened and the method of fastening the tissues. After use, the insertion section is removed from the operation section 1. Then, the operation section 1 is washed and sterilized so that it may be used again, while the insertion section is discarded. The operation section 1, which can be used together with any one of the various insertion sections 2A to 2D, is desirable from an economical point of view.

Tow pusher bars 21 and 22 and a pusher rod 89 (later described) extend through each of the insertion sections 2A to 2D. Whichever insertion section is connected to the operation section 1, it suffices to rotate the motor 7 in one direction by a predetermined angle to move the members 21, 22 and 89 in a specific manner; and it suffices to rotate the motor 7 first in one direction by a prescribed angle and then in the reverse direction by a predetermined angle to move the members 21, 22 and 89 in another specific manner. The direction in which to rotate the motor 7 and any angle by which to rotate the motor 7 can be set by means of the control circuit 12.

when the clipper 2A is used in combination with the operation section 1, the strokes of the pusher bar 21 and 22 are set at about 10 mm and about 30 mm, respectively. When the stapler 2B is coupled to the operation section 1, the stroke of the pusher rod 89 is set at about 20 mm. When the linear cutter 2C is attached to the operation section 1, the strokes of the pusher bars 21 and 22 are set at about 20 mm and about 30 mm, respectively. When the circular stapler 2D is used together with the operation section 1, the stroke of the pusher rod 89 is set at about 5 mm.

For simplicity of description, the pusher rod 89 will be described as a component different from the pusher bars 21 and 22. Nevertheless, the pusher rod 89 can be replaced by one of the pusher bars 21 and 22 in practice.

Figure 7:
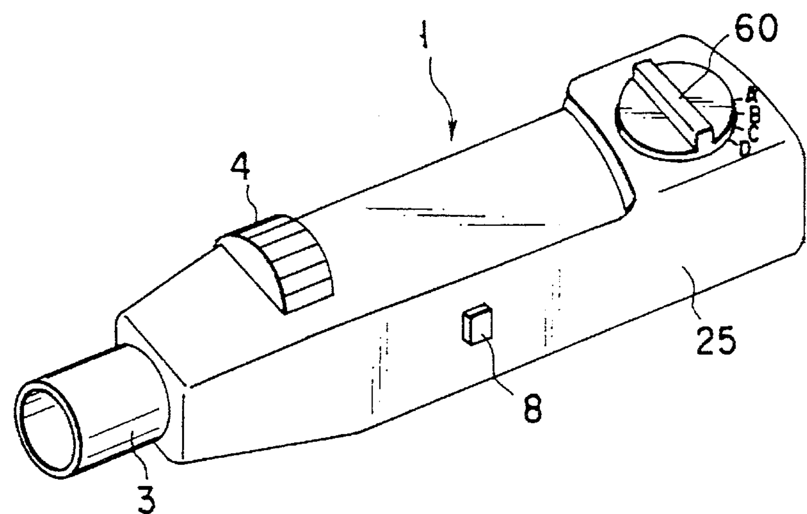
FIG. 7 is a perspective view of the operation section of a tissue-fastening device which is a second embodiment of the invention and which has a stroke/force adjusting mechanism.
Figure 8:
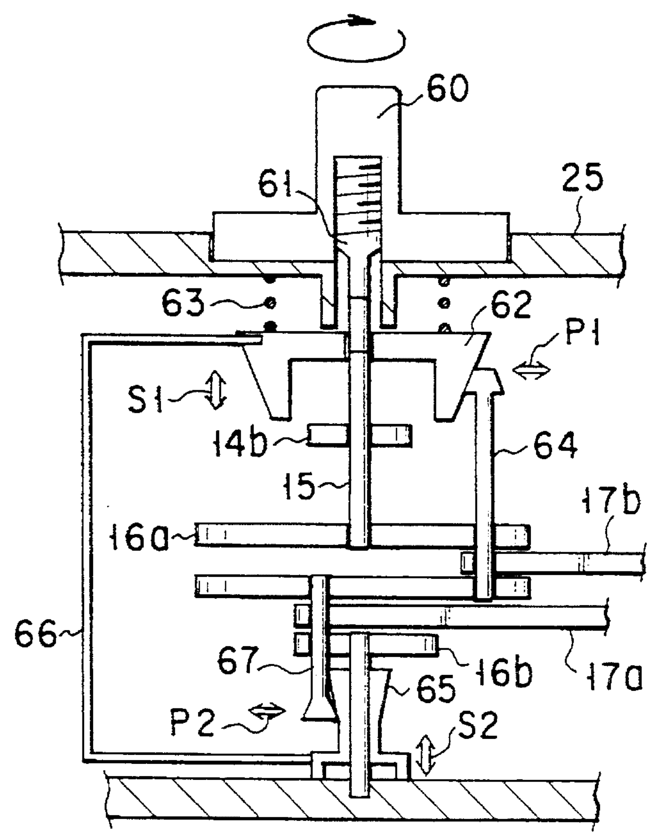
FIG. 8 is a sectional view of the stroke/force adjusting mechanism incorporated in the device shown in FIG. 7.
Figure 9:
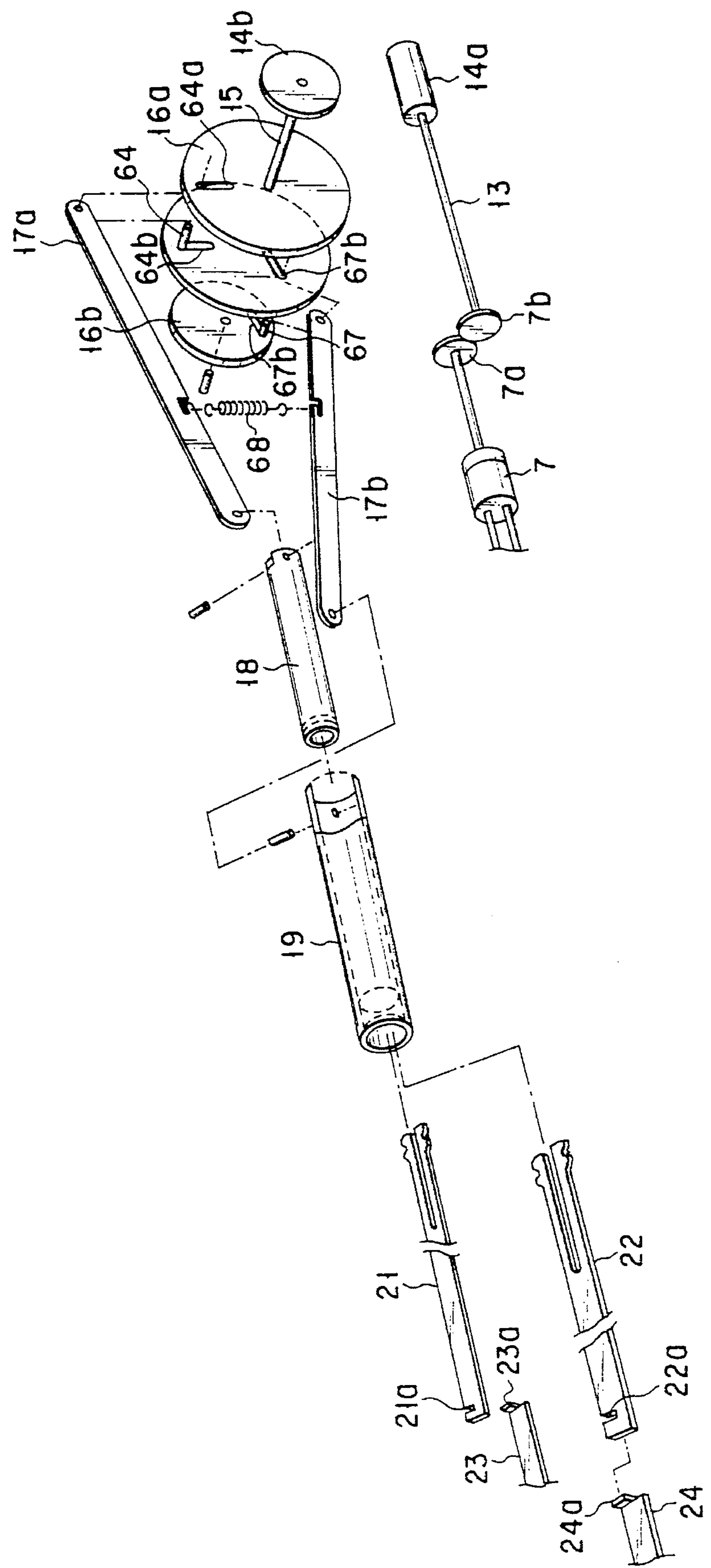
FIG. 9 is an exploded view of the electrically driven mechanism which is used in combination with the stroke/force adjusting mechanism shown in FIG. 8.

FIGS. 7, 8 and 9 shows a tissue-fastening device which is a second embodiment of the invention and which has a stroke/force adjusting mechanism. As shown in FIG. 7, a stroke-adjusting knob 60 is provided on the operation section 1. The knob 60 is rotated to select strokes and toques suitable for the type of the insertion section 2 attached to the operation section 1.

The stroke-adjusting knob 60 is connected to an extension of the drive shaft 15; it is positioned coaxial with a drive shaft 15. The extension of the shaft 15 has a thrust screw 61. A conical cam 62 is secured to the distal end of the thrust screw 61. A first spring 63 is compressed between the conical cam 62 and inner surface of the casing 25. A first pin 64 connects a first pusher link 17*a* and a first pulley 16*a*. The first pin 64 abuts at one end on the conical cam 62. Another conical cam 65 is arranged coaxial with the conical cam 62, opposing the same. The cam 65 is connected to the cam 62 by a link 66. A second pin 67 connects a second pusher link 17*b* and a second pulley 16*b*. The second pin 67 abuts at one end on the circumferential surface of the conical cam 64.

As shown in FIG. 9, a coil spring 68 is connected at one end to the first pusher link 17*a*, and at the other end to the second pusher link 17*b*. The first pulley 16*a* has a hole 64*a* elongated in the radial direction. Similarly, the second pulley 16*b* has a hole 67*a* elongated in the radial direction. A disc 16*c* has two holes 64*b* and 67*b*, both elongated in the radial direction. The first pin 64 has its end portions loosely fitted in the elongated holes 64*a* and 64*b*, whereas the second pin 67 has its end portions loosely fitted in the elongated holes 67*a* and 67*b*. The points where the pusher links 17*a* and 17*b* coupled to the pulleys 16*a* and 16*b*, respectively, can thereby be shifted in the radial direction of the pulleys 16*a* and 16*b*.

When the stroke-adjusting knob 60 is rotated, the conical cam 62 is moved along its axis in the direction of arrow S1 as shown in FIG. 8, pushing the first pin 64 outwards in the radial direction of the first pulley 16*a*, namely in the direction of arrow P1. At the same time, the conical cam 65, which is connected to the cam 62 by the link 66, is moved along its axis in the direction of arrow S2, pushing the second pin 64 outwards in the radial direction of the second pulley 16*b*, namely in the direction of arrow P2. The radii of circles in which the pins 64 and 67 rotate are thereby changed, thereby changing the strokes of the pusher links 17*a* and 17*b*, i.e., the distances the links 17*a* and 17*b* may move along the axis of the operation section 1.

The tapered circumferential surfaces of the conical cams 62 and 65, i.e., the cam surfaces, can have various shapes so that the cams 62 and 65 may serve to adjust the strokes of the pusher links 17*a* and 17*b* in one manner or another. Furthermore, a dial 59 may be placed around the knob 60 so that a surgeon may accurately set the strokes of the links 17*a* and 17*b* and also the drive forces on the links 17*a* and 17*b* at any values that are appropriate for the type of the insertion section 2 attached to the operation section 1.

The adjustment of the strokes and drive forces of the pusher links 17*a* and 17*b*, which is accomplished by rotating the knob 60, results in three advantages. First, once the strokes and drive forces of both pusher links are adjusted to desired values, staples can be applied to body tissues more readily and reliably than otherwise. Second, the tissue-fastening device may be combined with a centralized control system for an operating room, and a robotic surgery unit, to constitute an automatic tissue-fastening system. Third, the tissue-fastening device can be rendered "intelligent," provided that the insertion section 2 has a detector capable of determining the type of any body tissue and that the control section 1 has an electronic control unit for controlling the motor 7 in accordance with a signal output from the detector.

A tissue-fastening device, embodying the idea shown in conjunction with FIG. 7 to 9, will be described with reference to FIGS. 24 and 25. FIG. 24 is a sectional view showing the operation section of the device and also a part of the insertion section thereof, and FIG. 25 is a block diagram of the electric drive unit incorporated in the operation section. As shown in FIG. 24, the operation section 210 comprises a casing 212. It further comprises a identification circuit 220, a control circuit 222, a power supply 24 and an electric motor 226—all incorporated in the casing 212.

The rotation of the shaft of the motor 226 is transmitted to a drive shaft 228 via a first gear 230, a second gear 232, a lack 234 and a pinion 236. Two pulleys 238 and 240 are mounted on the drive shaft 228. Two pusher links 242 and 244 are coupled at one end to the pulleys 238 and 240, respectively, and at the other end to two pusher tubes 246 and 248, respectively. The first pusher tube 246 can move back and forth in the first pusher tube 248, and the second pusher tube 248 can move back and forth in a hollow cylindrical guide 250. A first pusher bar 252 is connected to the distal end of the first pusher tube 246, and a second pusher bar 254 to the distal end of the second pusher tube 248. Both pusher bars 252 and 254 extend into a hollow cylinder 218 through a spacer 256 which is fitted in the distal end portion of a drive ring 214. An elastic seal 258 is connected to the front of the spacer 256. The drive ring 214 has a sliding portion, on which an O-ring is mounted.

Each of the of pusher bars 252 and 254 has a notch at its distal end portion. Removably set in the notch of the first pusher bar 252 is a connecting flange formed integral with the rear end of a first pusher 214 provided in the insertion section 101. Removably set in the notch of the second pusher bar 254 is a connecting flange formed integral with the rear end of a second pusher 216 placed in the housing 201 of the insertion section 200. A button 212 is mounted on the housing 201. When pushed, the button 212 will release the pusher bars 252 and 254 from the notches of the first and second pushers 214 and 216.

A plurality of pins 264 protrude from the inner circumferential surface of the drive ring 214, which is set in sliding contact with the housing 201 of the insertion section 200. The pins 264 are electrically connected to the identification circuit 220 by a signal cable 266 and a slip ring (not shown). As shown in FIG. 25, the pins 264 consist of four identification pins 264*a* to 264*b* and one common pin 264*e*. Five contacts (not shown) are mounted on the proximal end portion of the housing 210. The contacts remain in touch with the pins 264, respectively, while the insertion section 200 remains fastened to the operation section pins 264. The contacts consists of one common contact and four identification contacts, one of which is connected to the common contact by a conductor. which identification contact is electrically connected to the common contact depends on the type of the insertion section 200.

The identification circuit 220 is designed to determine which identification contact is electrically connected to the common contact. Since the insertion section 200 has four identification contacts, the circuit 220 can determine which one of four types the section 200 happens to be.

The two pushers of each of the insertion sections 2A, 2B, 2C and 2D may have the same stroke. In this case it is possible to move both pushers by driving the motor 226 in one direction only. If the pushers of each insertion section have different strokes, they are moved by driving the motor 226 in the forward direction and the reverse direction, through a predetermined angle. The electric motor 226 is driven, either in one direction only or in both directions, by the drive circuit 223 which operates in accordance with control signals supplied from the control circuit 222. The rotation of the shaft of the motor 226 is detected by the encoder 225, which generates signals representing the rotation. These signals are supplied to the control circuit 222. From these signals the circuit 222 generates control signal, which are supplied to the drive circuit 223.

Figure 10:
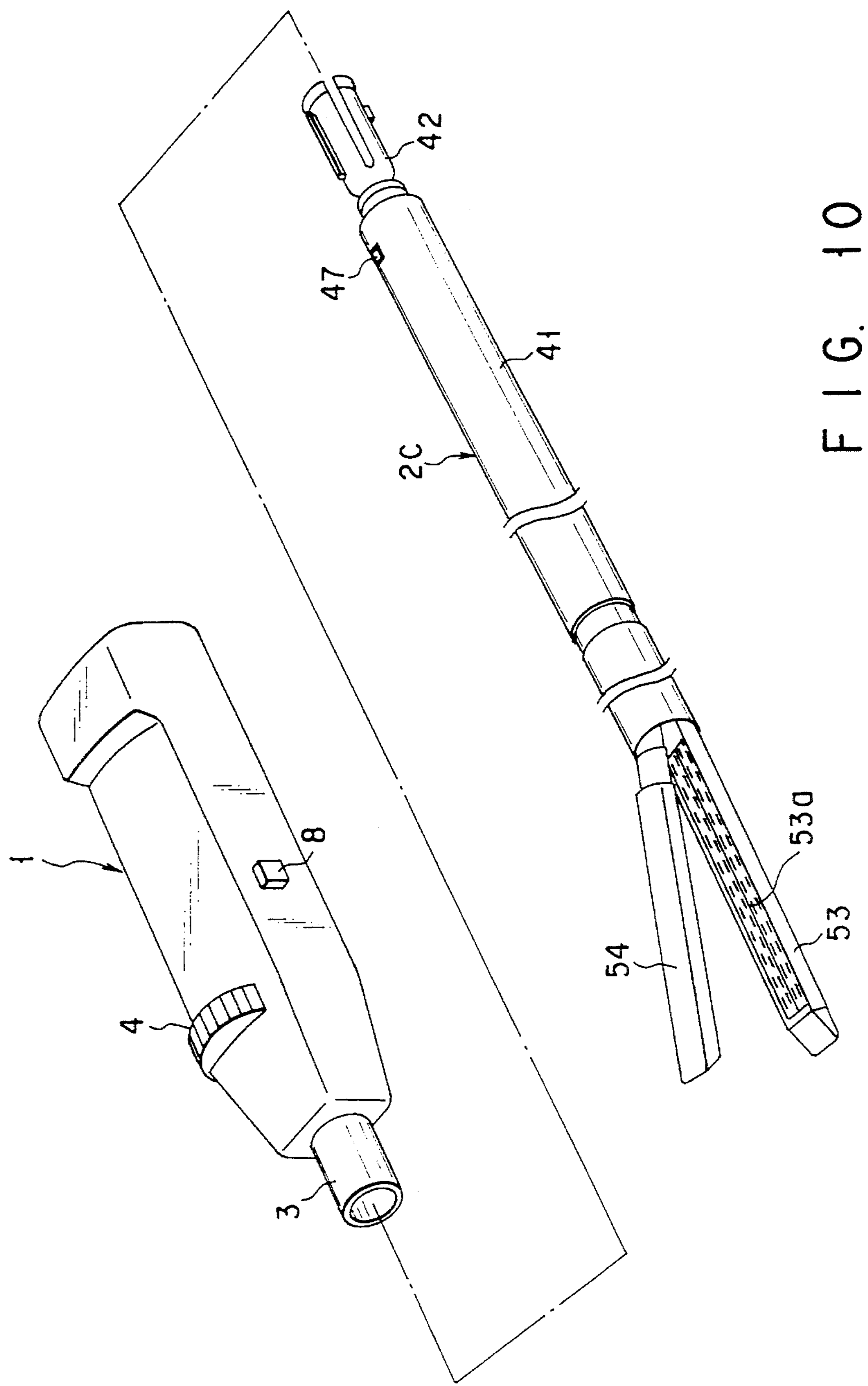
FIG. 10 is an exploded view of a tissue-fastening device according to a third embodiment of the present invention.
Figure 13:
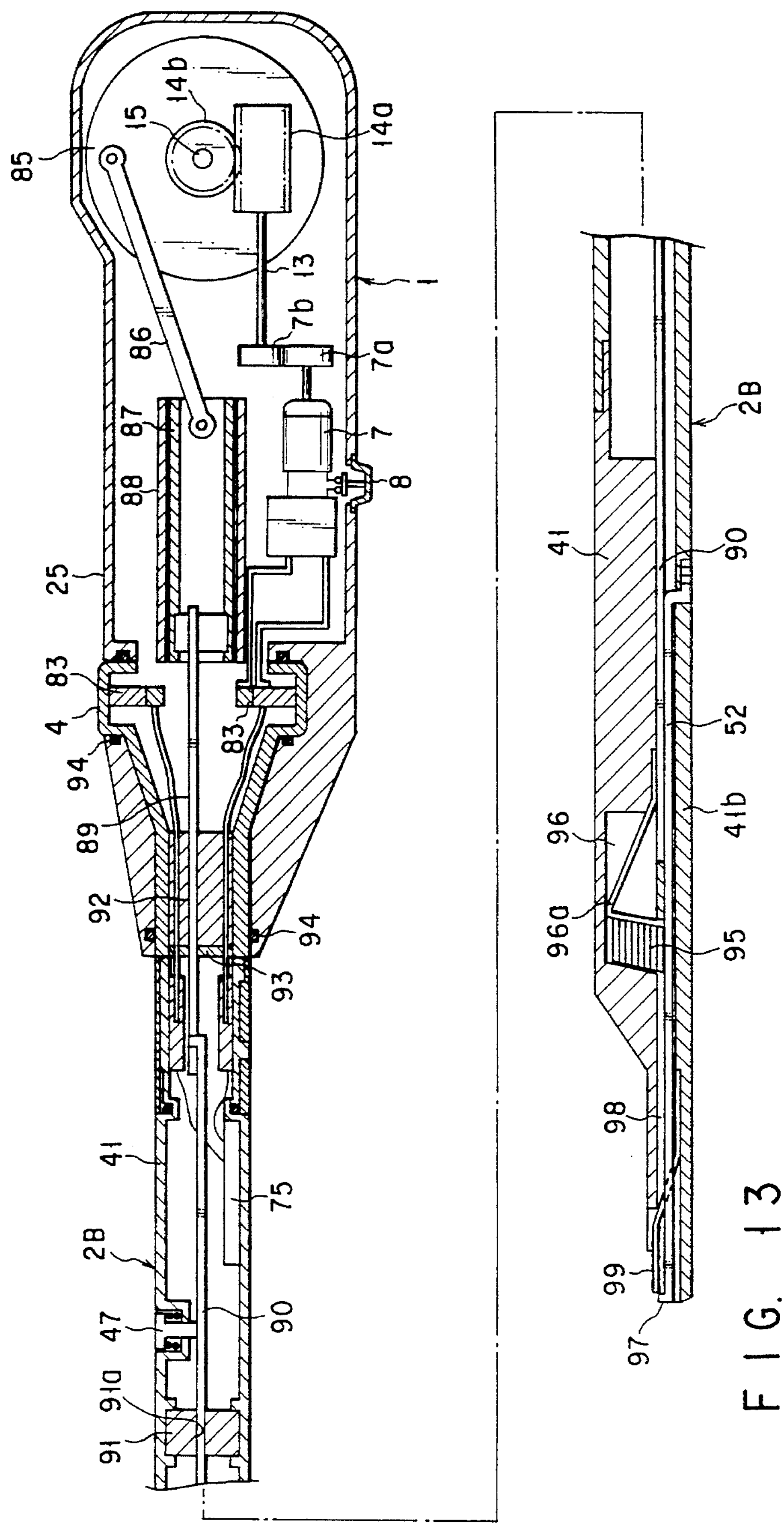
FIG. 13 is an exploded, longitudinal sectional view of a tissue-fastening device according to a fourth embodiment of the present invention.

FIGS. 10, 11 and 13 show a tissue-fastening device which a third embodiment of the present invention. FIG. 10 illustrates the entire device. As can be understood from FIG. 10, the operation section 1 of this device is basically the same as that of the first embodiment. An insertion section 2C is removably coupled to the operation section 1. The insertion section 2C is either a linear stapler or a linear cutter.

Figure 12:
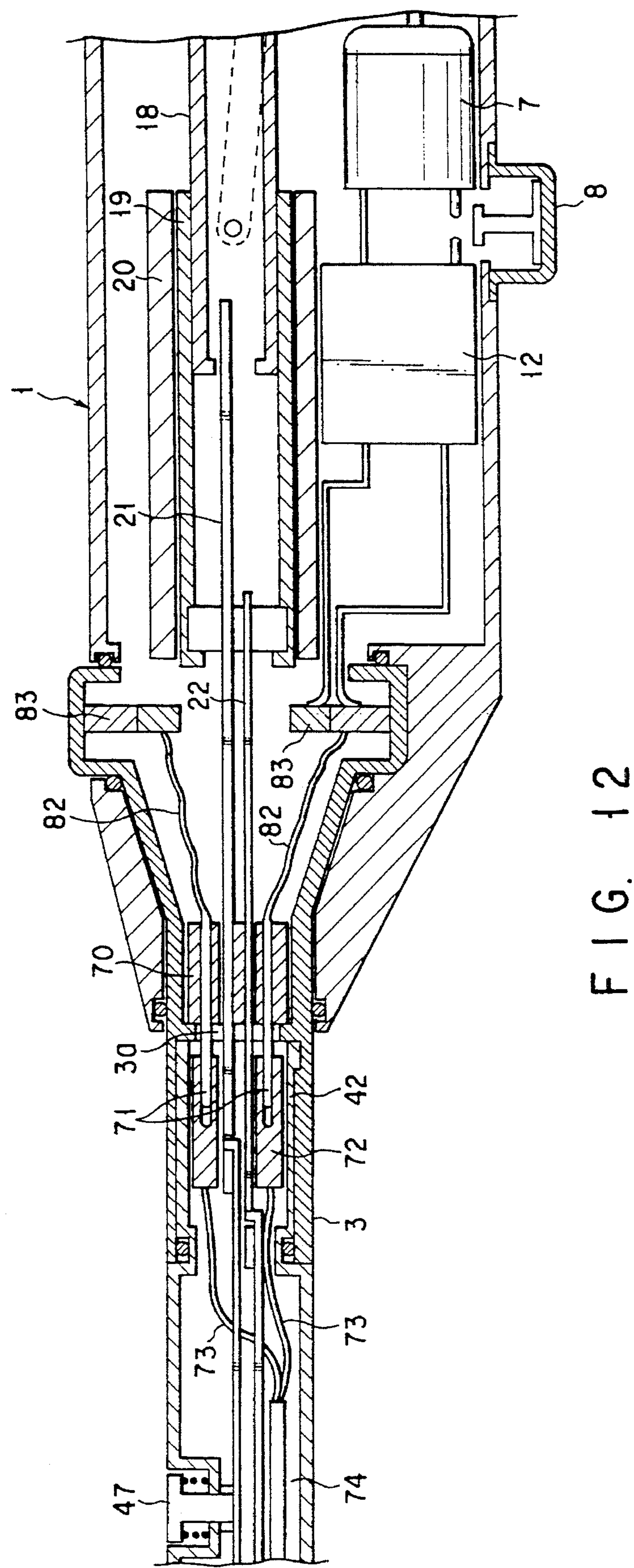
FIG. 12 is a longitudinal sectional view of the operation section of the device shown in FIG. 10.

As shown in FIG. 12, a plurality of terminal pins 71 are held by an insulator 70 fitted in the first connector 3 of the operation section 1. They extend through the first connector 3, piercing the seal member 3*a* of the first connector 3. The thin, proximal end portion 42 of the section 2a has a socket 72. When the proximal end portion 42 is inserted into the first connector 3 of the operation section 1, the terminal pins 71 are inserted into the socket 72 and, hence, electrically connected to the socket 72. The socket 72 is electrically connected by a cable 73 to a conductor 74 located in the insertion section 2C.

As illustrated in FIG. 11, the conductor 74 is connected to a power source 75, which is a battery loaded in a cartridge 53 removably attached to the distal end of the insertion section 2C. The cartridge 53 contains many staples 76, a staple pusher 77 for pushing the staples 76 forward, a staple pusher bar 78 for pushing the pusher 77 upwards, and a cutter 79 for cutting body tissues along a train of staples 76 applied to the tissues. As shown in FIG. 12, the cartridge 53 has, at its proximal end portion, a contact 80 which is connected by a cable 81 to the conductor 74 (FIG. 11).

In the operation section 1 there is provided a brush electrode 83 which is electrically connected, at one end, to the terminal pins 71 by a lead wire 82. The other end of the brush electrode 83 is connected to a control circuit 12 located in the operation section 1. An electric current can be supplied from the power supply 75 contained in the cartridge 53 to an electric motor 7 incorporated in the operation section 1, through the cable 81, the conductor 74, the socket 72 and the terminal pins 71. It should be noted that the pins 71 and the socket 72 are arranged in the first connector 3.

In the third embodiment, the operation section 1 need not have a space for accommodating the power supply 75 and can, therefore, be smaller than otherwise. Since the cartridge 53, which contains the power supply 75, is replaced by a new one after the staples 76 have been applied to body tissues, the power supply 75 suffices to provide electric power barely enough to accomplish one stapling operation. The power supply 75 can therefore be small and need not be recharged at all.

FIGS. 13 and 14 show a tissue-fastening device which a fourth embodiment of the present invention and which comprises an operation section 1 and a stapler 2B coupled to the section 1. Like its counterpart of the first embodiment, the operation section 1 comprises a casing 25, a control circuit 12 and an electric motor 7. The circuit 12 and the motor 7 are located in the casing 25. The drive force of the motor 7 is transmitted to a drive shaft 15 by pinions **7*a* and 7*b*, a worm gear 14*a* and a worm wheel 14*b*. A pulley 85 is mounted on the drive shaft 15. A shaping blade pusher link 86 is pivotally connected, at one end, to the pulley 85. The other end of the pusher link 86 is coupled to a pusher tube 87, which is supported by a guide 88 and which can slide along its axis. A pusher rod 89 is connected to the distal end of the pusher tube 87 and can rotate on its axis. The pusher rod 89 is set in engagement with a shaping blade 90 which is provided in the stapler 2B. The shaping blade 90 can slide back and forth, with its middle portion loosely inserted in a guide hole 91*a* of a seal block 91 which is located in the proximal end portion of the stapler 2B. The seal block 91** is coated with silicone grease.

The operation section 1 contains a drive ring 4 which can rotate. A spacer 92 and an elastic seal 93 are provided within the drive ring 4. The section has a first connector 3, to which the housing 41 of the stapler 2B is removably coupled. O-rings 94 are located between the sliding surface of the drive ring 4 and that of the casing 25, rendering the casing 25 watertight.

In the distal end portion of the stapler 2B there are provided a staple cartridge 96, an anvil 52, the shaping blade 90, a staple passage 98 and a staple-ejecting spring 99. The cartridge 96 contains a plurality of staples 95 each having a U-shaped cross section. The anvil 52 has, at one end, a flange 96 designed to deform staples 95 into closed ones. The shaping blade 90 is arranged above the anvil 52. Through the staple passage 98 the staples 95 are pushed toward the anvil 52. The staple-ejecting spring 99 is located in the vicinity of the flange 97 of the anvil 52 and is used to eject a staple 95 outwardly through the opening **41*a* of the housing 41. Arranged in the housing 41 of the stapler 2B is a base plate 41*b* which supports the cartridge 96, the anvil 52, the shaping blade 90 and the staple-ejecting spring 99**.

The shaping blade 90 has a pair of projections **90*a* and 90*a* at its distal end. The projections 90*a* and 90*a* push the staples, one after another, toward the opening 41*a* of the housing 41. At this time, all staples 95 in the cartridge 96 are biased by a spring 96*a* toward the base plate 41**.

In all other respects, the tissue-fastening device according to the fourth embodiment is the same as the device according to the first embodiment.

Figures 15A, 15B, 15C:
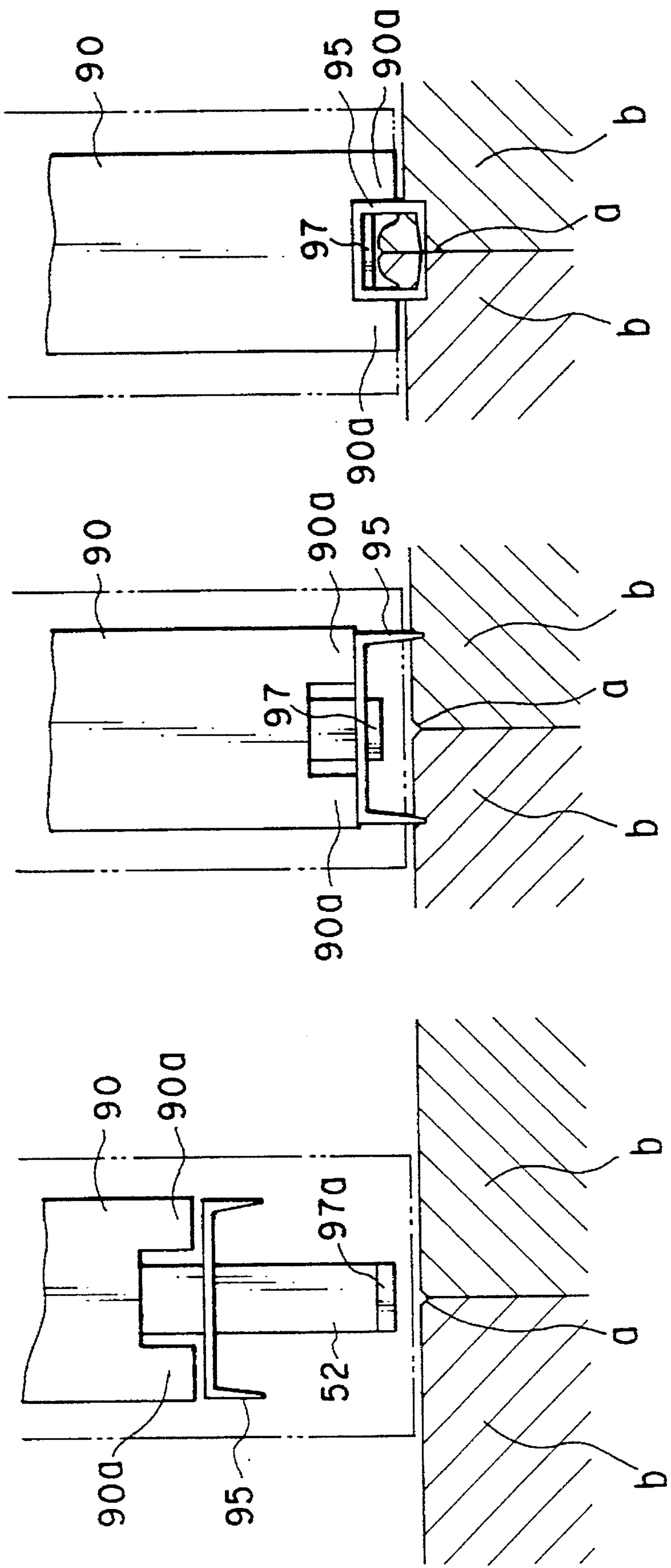
FIGS. 15A to 15C are views explaining how the staple applicator is driven which is provided in the distal end portion shown in FIG. 14.

With reference to FIGS. 15A to 15C, it will be explained the stapler 2B is operated to apply staples 95 to the severed portions a of two body tissues b, thereby to fasten the tissues b together. First, a surgeon holds the tissues b together, by using a forceps (not shown). Then, he or she places the distal end of the stapler 2B at the severed portions which abut on each other. This done, an electric current is supplied from an external power supply 75 to the motor 7 via brush electrodes 83 and lead wires 82. As the motor 7 is driven, the pulley 85 is rotated, sliding the pusher tube 87, the pusher rod 89 and the shaping blade 90 toward the distal end of the stapler 2B.

As shown in FIG. 15A, as the shaping blade 90 so slides, its projection **90*a* moves the lowermost staple 95 toward the distal end of the stapler 2B. Then, as shown in FIG. 15B, the shaping blade 90 pushes the staple 95 to the flange 97 of the anvil 52, while pressing the staple-ejecting spring 99 (FIGS. 13 and 14) onto the base plate 41*b*. As a result, the legs of the staple 95 pierce into the tissues b. The staple 95 now has its middle portion held by the flange 97 of the anvil 52. Thus, both end portions of the staple 95 are bent as the shaping blade 90 further pushes the staple 95. The shaping blade 90 pushes the staple 95 until the legs of the staple 95 abut on each other, thereby fastening the tissues b together, as shown in FIG. 15C. Thereafter, the shaping blade 90 is pulled backward, and the staple-ejecting spring 99 ejects the staple 95, thus deformed, from the opening 41*a* (FIG. 14) of the housing 41. Then, the stapler 2B assumes its initial condition and is ready to apply the next staple 95**.

Physiological salt solution and the patient's body fluids may wet the operation section 1 during the use of the tissue-fastening device. Nonetheless, the elastic seal 93 and the O-rings 94, all provided on the section 1, prevent the solution and body fluids from entering the operation section 1.

Thanks to the use of the motor 7 which drives the stapler 2B to fasten body tissues together, the tissue-fastening device has high operating efficiency. The stapler 2B drives staples 95 into tissues and bend them, with the same force, when the device is manipulated by any surgeon.

Figure 16:
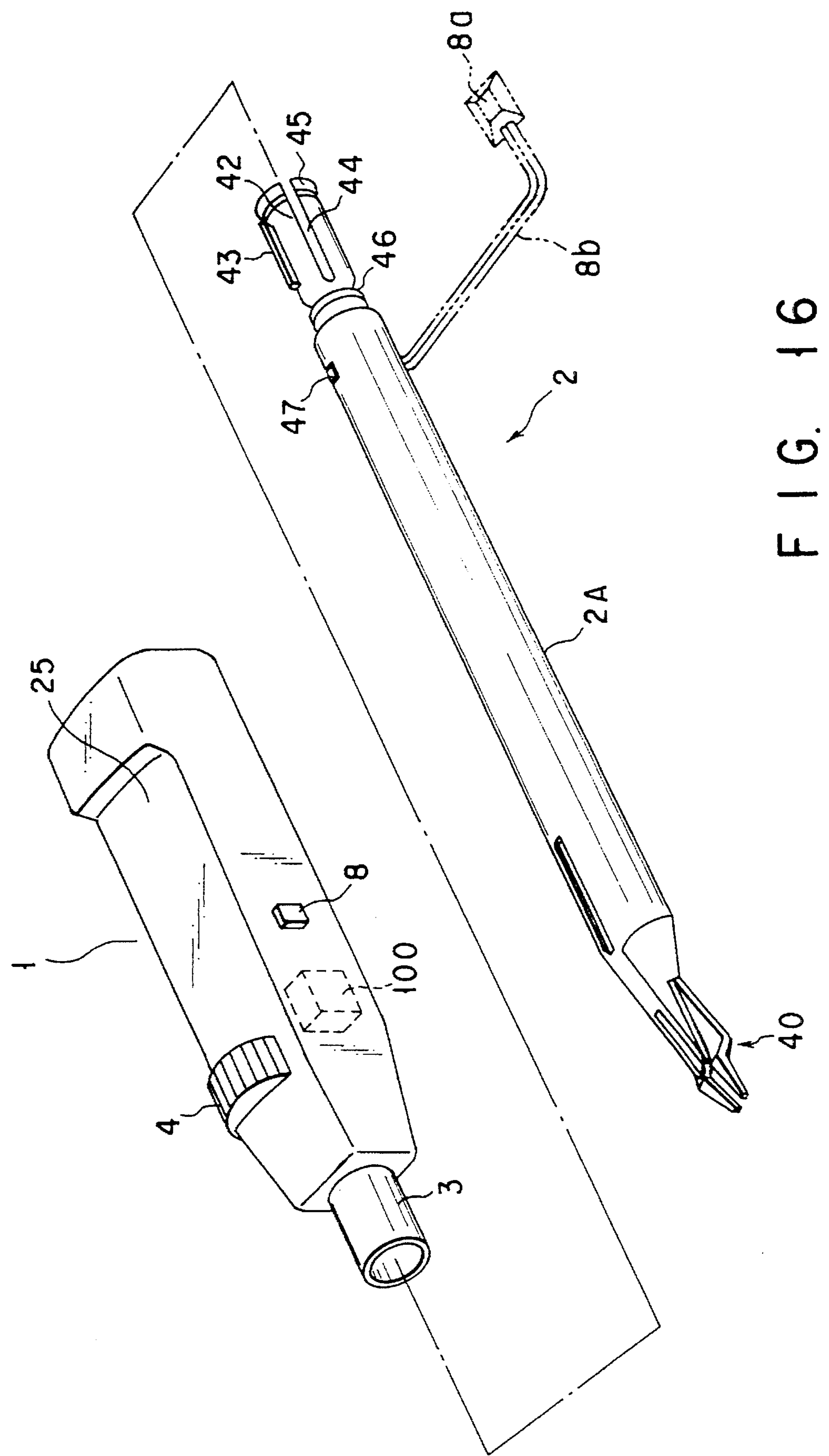
FIG. 16 is an exploded view of a tissue-fastening device according to a fifth embodiment of the present invention.
Figure 17:
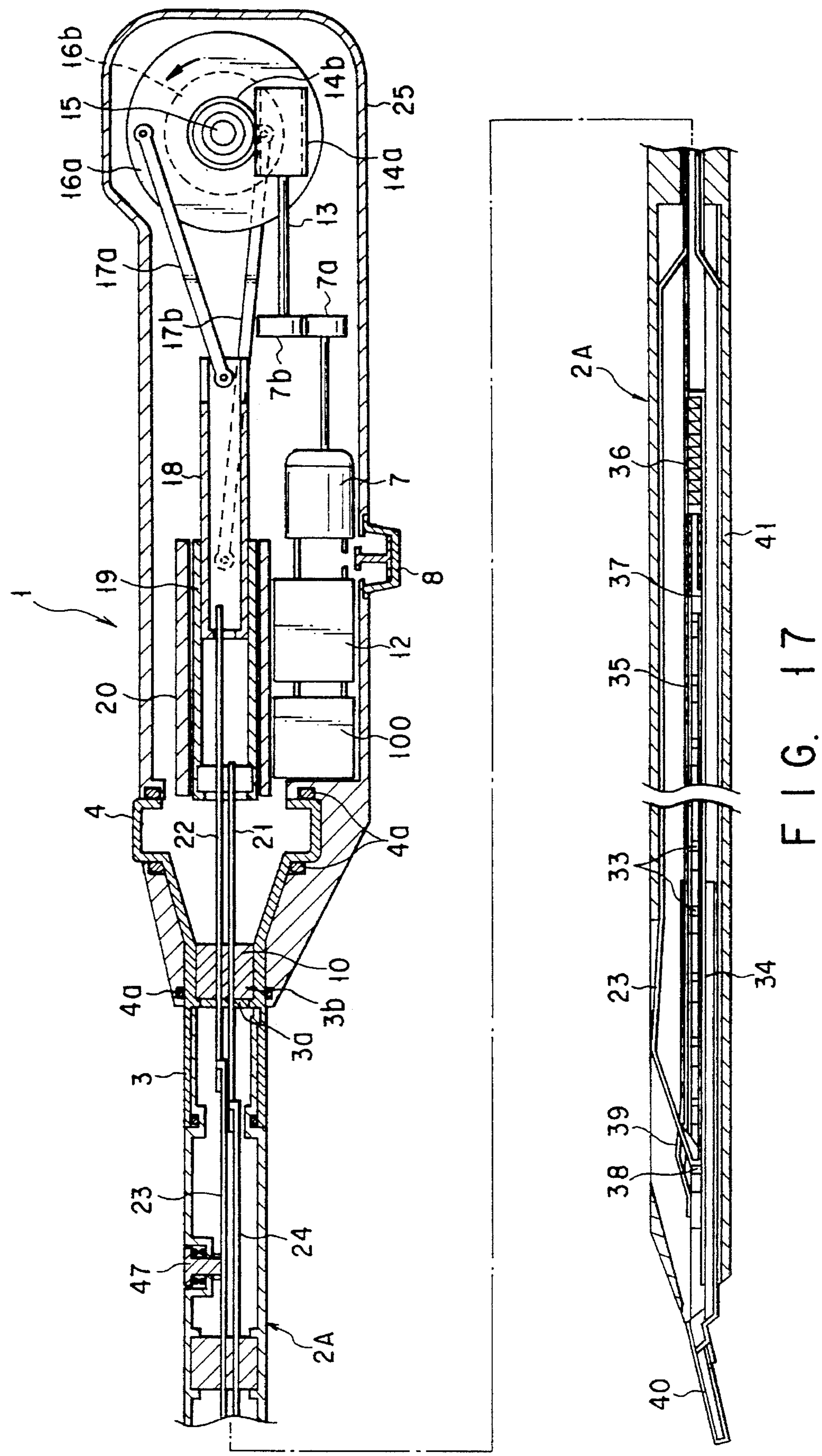
FIG. 17 is an exploded, longitudinal sectional view of the tissue-fastening device shown in FIG. 16.

FIGS. 16 and 17 show a tissue-fastening device which a fifth embodiment of the present invention. As is seen from FIG. 16, this device comprises an operation section 1 and a clipper 2A. The clipper 2A is removably coupled to the first connector 3 of the section 1 and designed to collapse and close a portion of a tubular organ. The clipper 2A can be rotated on its axis when the drive ring 4 of the operation section 1 is rotated, and can be driven when the switch 8 of the section 1 is operated.

As shown in FIG. 17, the first connector 3 of the operation section 1 is closed by a seal member **3*a*. Hence, the casing 25 of the operation section 1 is sealed in its entirety. Contained in the casing 25 are an electric motor 7, a control circuit 12 and a power supply 100. The motor 7 is, for example, a stepping motor, and the power supply 100 is, for example, a lithium cell. The control circuit 12 controls the power from the power supply 100 to change the drive force and rotational speed of the motor 7**.

The fifth embodiment is basically the same as the first embodiment shown in FIGS. 1 to 4, except that the power supply 100 cannot be removed from the casing 25 to be replaced with a new one. Therefore, for simplicity of description, the structure of the fifth embodiment will not be described in detail.

Since the motor 7 and the power supply 100 are contained in the operation section 1, the clipper 2A can be driven by electric drive means to collapse and close a portion of a tubular organ. A surgeon need not exert a large force to operate the device and will not be tired so much as otherwise. In addition, the device has high operating efficiency. Since the power supply 100 is contained in the casing 25, no connector cable needs to be used to connect the operation section 1 to an external power supply. The surgeon who is manipulating the device is free from hindrance which may be caused by the use of a connecting cable.

Blood and washing solutions may wet the operation section 1 during the use of the tissue-fastening device, but they are prevented from entering the section 1 by the seal member 3*a* and an O-ring 4*a*. To wash and sterilize the operation section 1 after the use of the tissue-fastening device, the clipper 2A is detached from the operation section 1. Then, blood, if any, is washed away from the operation section 1. The section 1 is sterilized with high-pressure steam or ethylene oxide gas (EOG), so that it may be used again in combination of a new clipper 2A. This serves to reduce medical fees for collapsing a tubular organ and close the same with clips.

Driven by the electric motor 7, the clipper 2A can apply and bend clips always with a constant force. The clipper 2A can be rotated on its axis by rotating the drive ring 4, to thereby orientate a jaw 40 in a desired direction.

The seal member 3*a* and the O-ring 4*a* may be made of material containing shape-memory resin. The shape memory resin will expand as heat is applied to the seal member 3*a* and the O-ring 4*a* while the operation section 1 is being sterilized with high-pressure steam or ethylene oxide gas (EOG). Both the seal member 3*a* and the O-ring 4*a* will have their sealing efficiency increased. The operation section 1 can therefore be sterilized thoroughly, with its internal components not affected by the sterilizing steam or gas.

A clutch may be connected across the first pulley 16*a* and the second pulley 16*b* both arranged in the casing 25 of the operation section 1, for transmitting drive force between these pulleys 16*a* and 16*b*. In this case, it is possible to actuate the clip-feeding mechanism and clip-bending mechanism of the device, independently of each other. This helps to enhance the operating efficiency of the tissue-fastening device.

Furthermore, the drive force can be transmitted to the clip-feeding mechanism and the clip-bending mechanism under the control of a CPU so that both mechanism may be driven with optimal timing.

Still further, as shown in FIG. 16, a remote switch 8*a* may be connected to the clipper 2A by a cable 8*b* which extends from the housing 41 of the clipper 2A. The remote switch 8*a* is used in place of the switch 8 on the operation section 1, for starting and stopping the electric motor 7. A socket (not shown), which is electrically connected to the motor 7 and the control circuit 12, both provided in the housing 41, may be mounted on the housing 41, and the remote switch 8*a* may be connected to the socket by the cable 8*b*. If this is the case, the remote switch 8*a* can be located at the position best to the surgeon who manipulate the tissue-fastening device.

Figure 18:
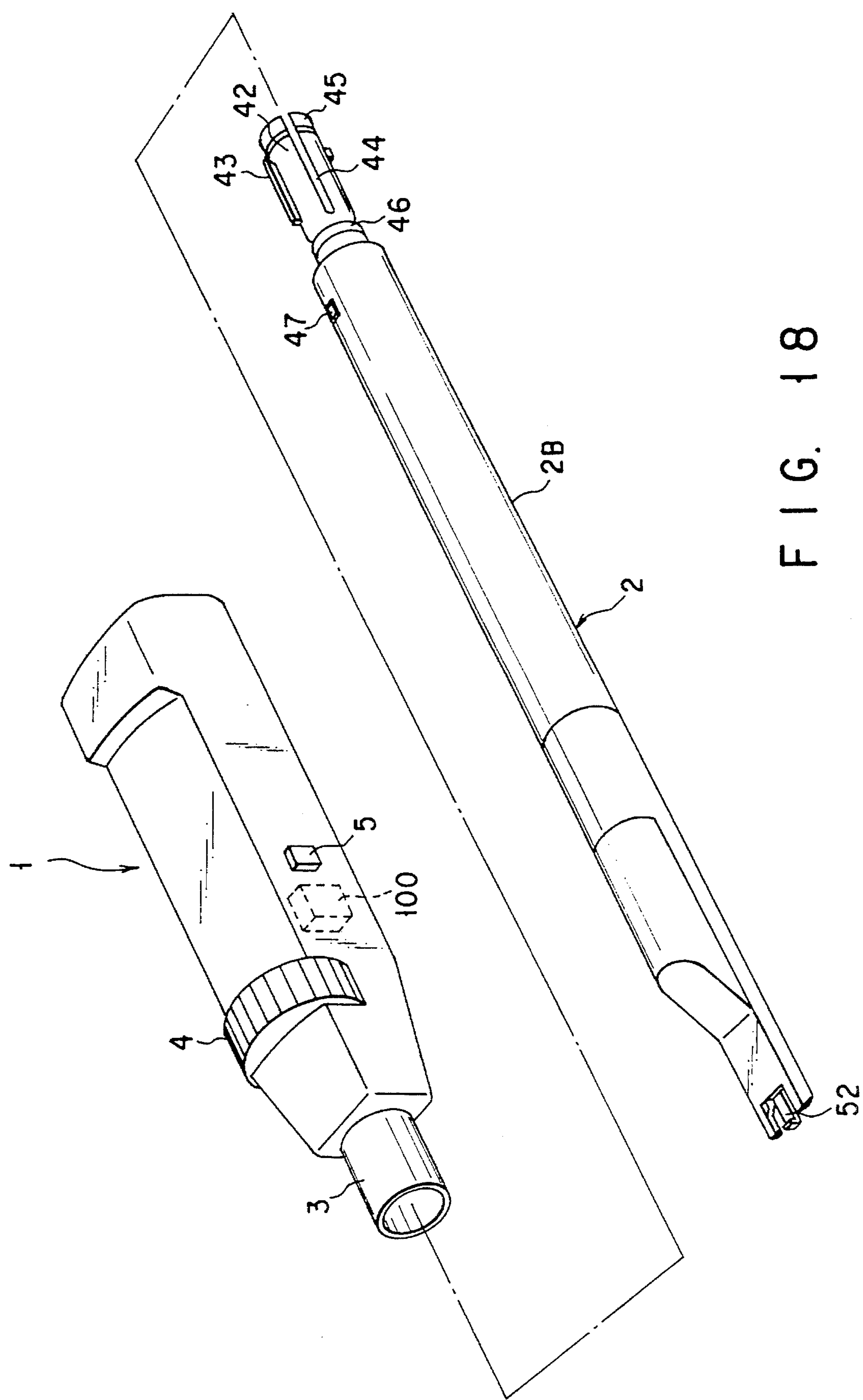
FIG. 18 is an exploded view of a tissue-fastening device according to a sixth embodiment of the present invention.
Figure 19:
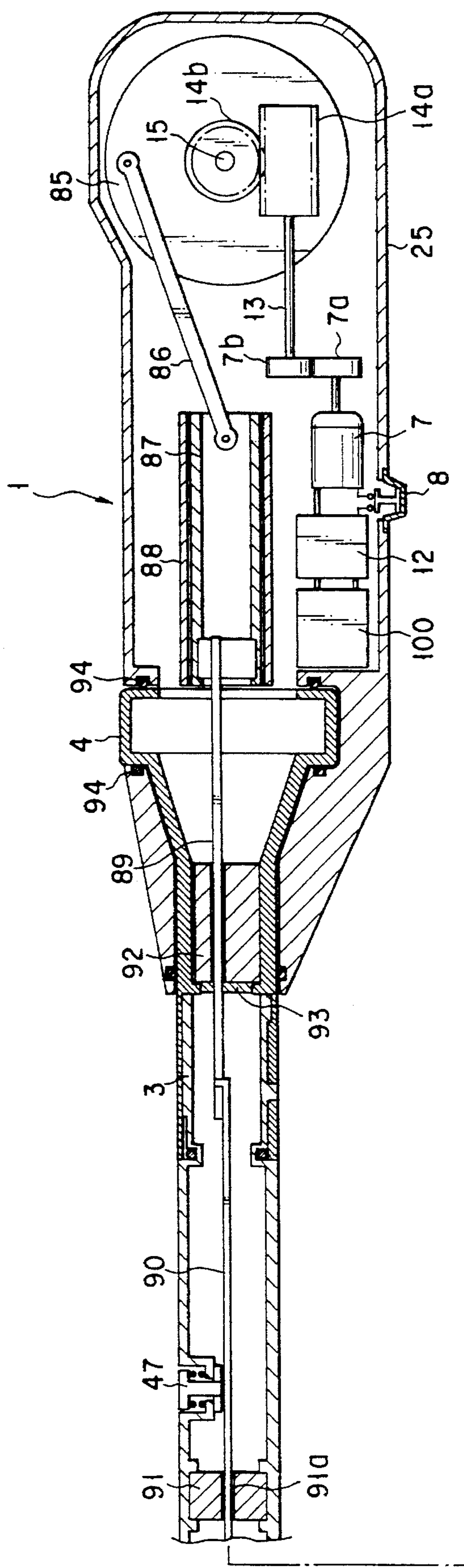
FIG. 19 is an exploded, longitudinal sectional view of the tissue-fastening device illustrated in FIG. 18.
Figure 19:
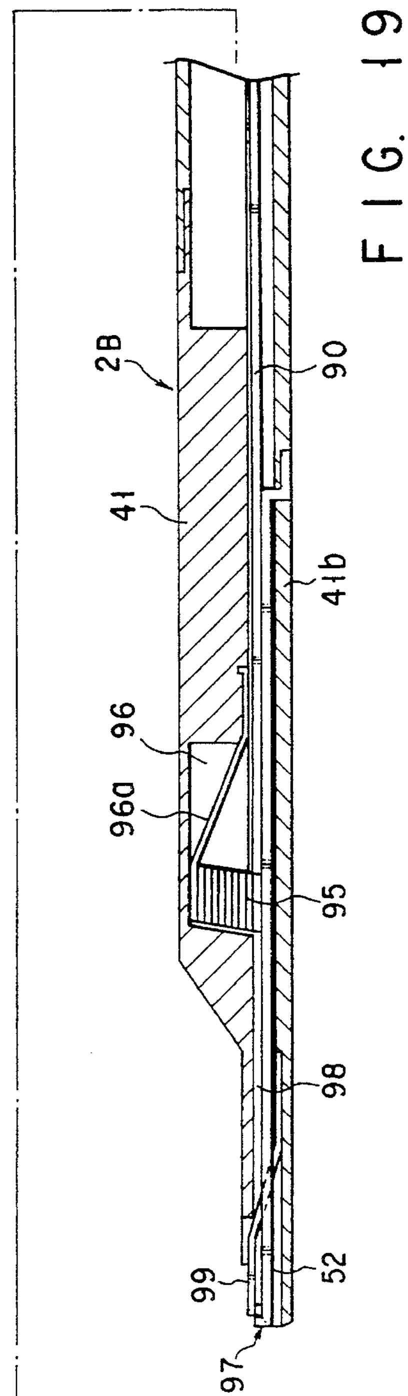

FIGS. 18 and 19 illustrates a tissue-fastening device which a sixth embodiment of the invention. The sixth embodiment is similar to the fifth embodiment, in that the casing 25 of the operation section 1 contains an electric motor 7, a control circuit 12 and a power supply 100. The motor 7 is, for example, a stepping motor, the power supply 100 is, for example, a lithium cell, and the control circuit 12 controls the power from the power supply 100 to change the drive force and rotational speed of the motor 7. The sixth embodiment is similar to the fourth embodiment, in that a stapler 2B is removably coupled to the distal end of the operation section 1.

The operation section 1 and the stapler 2B, constituting the sixth embodiment, are identical in structure and function to the operation section of the fifth embodiment and the stapler of the fourth embodiment, respectively. Therefore, the components similar or identical to those of the fourth and fifth embodiments will be described and are designated at the same numerals in FIGS. 18 and 19.

Figure 20:
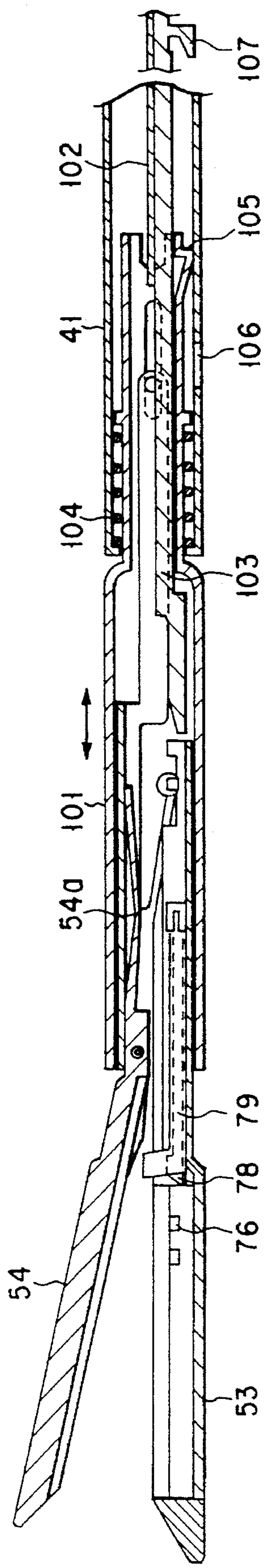
FIG. 20 is a longitudinal sectional view of the insertion section of a tissue-fastening device according to a seventh embodiment of this invention.

FIG. 20 shows the insertion section of a tissue-fastening device according to a seventh embodiment of the invention. More precisely, FIG. 20 illustrates a linear cutter 2C which is used as the insertion section of the device. The linear cutter 2C is basically identical in structure to the cutter shown in FIGS. 10 and 11. It is removably connected to the operation section (not shown) of the tissue-fastening device.

As shown in FIG. 20, an anvil 54 is rotatably coupled to the distal end of the linear cutter 2C. The anvil 54 is biased toward its open position by means of a spring 54*a*. Secured to the distal end of the linear cutter 54 is a cartridge 53 which contains two rows of staples 76. The cartridge 53 has a straight groove 53*a*, which extends between the rows of staples 76 as shown in FIG. 10. A cutter 79 is slidably rests in the groove 53*a*, for cutting body tissues after the tissues are fastened together with staples 76.

The linear cutter 2C has a hollow cylinder 101 having a thick portion and a thin portion. The thick portion loosely covers the distal end portion of the cutter 2C, whereas the thin portion is slidably inserted in the housing 41 of the cutter 2C. The rear end of the hollow cylinder 101 is connected to an anvil-driving bar 102 which extends through the housing 41. A staple pusher bar 78 extends through the distal end portion of the linear cutter 2C. Located at the rear of this bar 78 is a pushing member 103 which extends, partly through the distal end portion of the cutter 2C and mostly through the housing 41 of the cutter 2C. The anvil-driving bar 102 is coupled to a pusher rod 89 (to be described later) and can be moved back and forth in the housing 41 of the linear cutter 2C.

The hollow cylinder 101 is biased backward by a coil spring 104 inserted in the housing 41 and wound around the thin portion of the cylinder 101. An elastic stopper 105 at the rear of the cylinder 101. The housing 41 has, at its distal end portion, a hole 106 for holding a part of the stopper 105. At the back of the pusher member 103 there is provided a release member 107 which has a cam surface and which is designed to release that part of the stopper 105 from the hole 106 of the of housing 41.

How the linear cutter 2C is operated will be described below.

When the electric motor 7 (FIG. 17) incorporated in the operation section 1 is driven, the pusher rod 89 pushes the hollow cylinder 101 and the anvil-driving bar 102 toward the distal end of the cartridge 53. Thus pushed, the cylinder 101 closes the anvil 54. At this time the stopper 105 is held at its part in the hole 106 of the of housing 41. The anvil 54 is thereby held in closed state.

As the motor 7 is further driven, the pusher member 103 slides toward the distal end of the cartridge 53, pushing the cutter 79 and the staple pusher bar 78 forward. Thus pushed, the pusher bar 78 drives the staples 76 into the body tissues which are clamped between the cartridge 53 and the anvil 54. Next, the anvil 54 is further closed, deforming the staples 76. Thus deformed, the two rows of staples 76 fasten the tissues together, forming two seams. Simultaneously, the cutter 79, being driven forward, cuts the fastened tissues along a line extending between the two rows of applied staples 76.

when the cutter 79 reaches the distal end of the cartridge 53, the release member 107 of the pusher member 103 releases the stopper 105 from the hole 106 of the of housing 41. Then, the hollow cylinder 101 is moved backward, opening the anvil 54. Thus completes the fastening of tissues.

Figure 21:
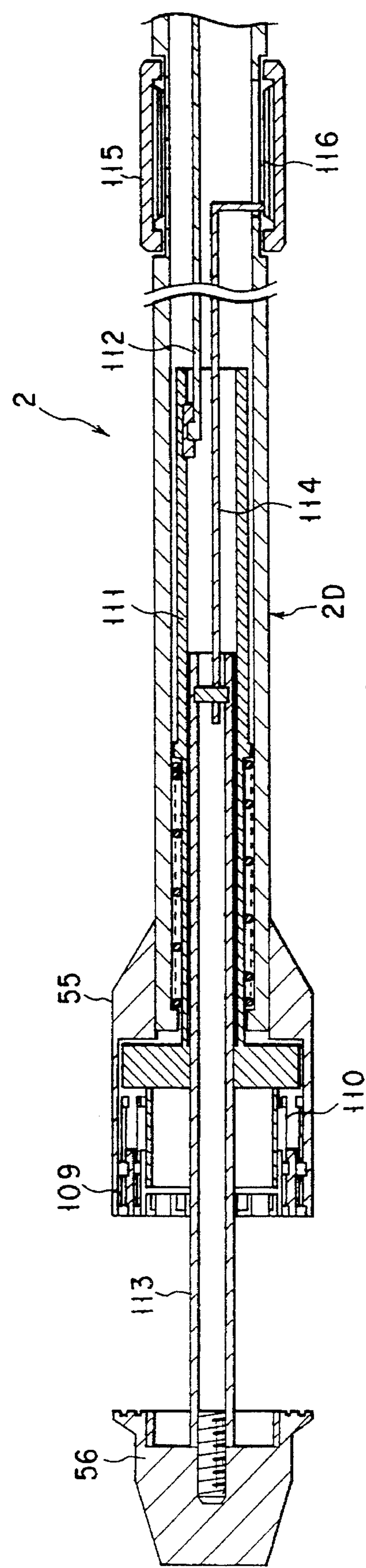
FIG. 21 is a longitudinal sectional view of the insertion section of a tissue-fastening device according to an eighth embodiment of the invention.

FIG. 21 illustrates the insertion section of a tissue-fastening device according to an eighth embodiment of this invention. To be more specific, FIG. 21 shows a circular stapler 2D which is used as the insertion section of the device. The circular stapler 2D is removably connected to the operation section (not shown) of the device, which is identical to that one shown in FIGS. 16 and 17, fastening device.

As shown in FIG. 21, a staple-ejecting section 55 and an anvil 56 are provided at the distal end of the circular stapler 2D. The staple-ejecting section 55 has a circular groove and a ring-shaped cutter 110 in its front. The groove holds a plurality of staples 109. The ring-shaped cutter 110 surrounds the circular groove and is concentric thereto. The anvil 56 is mounted on the distal end portion of an anvil shaft 113. The proximal end portion of the shaft 113 is slidably inserted in the cylindrical housing of the circular stapler 2D and is coupled to an anvil pusher 114. The anvil pusher 114 extends through the housing of the stapler 2D. The rear end of the pusher 114 is set in screw engagement with the screw portion 116 of an anvil-driving ring 115. The ring 115 is loosely mounted on the cylindrical housing of the circular stapler 2D. At the rear of the staple-ejecting section 55 there is provided a staple pusher 111. The staple pusher 111 is connected by a transmission member 112 to the operation section.

How the circular stapler 2D is operated will be explained below.

First, a surgeon manipulates the anvil 56, thereby inserting the anvil 56 into the severed ends portions of two tubular organs. Next, he or she rotates the anvil-driving ring 115, adjusting the space between the staple-ejecting section 55 and the anvil 56. The surgeon then drives the motor incorporated in the operation section, pushing the transmission member 112 forward. The member 112 in turn pushes the staple pusher 111 forward. The staple pusher 111 pushes the staples 109, which pierce into the severed ends portions of the organs clamped between the section 55 and the anvil 56. The staple pusher 111 is further moved forward, bending the staples 109 into closed ones. As a result, the severed end portions of the tubular organs are fastened together with the staples 109. Then, the ring-shaped cutter 110 cuts off the inner parts of the stapled end portions of the organs. Then, the surgeon rotates the anvil-driving ring 115 in the opposite direction, spacing the anvil 56 away from the staple-ejecting section 55. The fastened end portions of the tubular organs are thereby released from the nip between the section 55 and the anvil 56.

Figure 23:
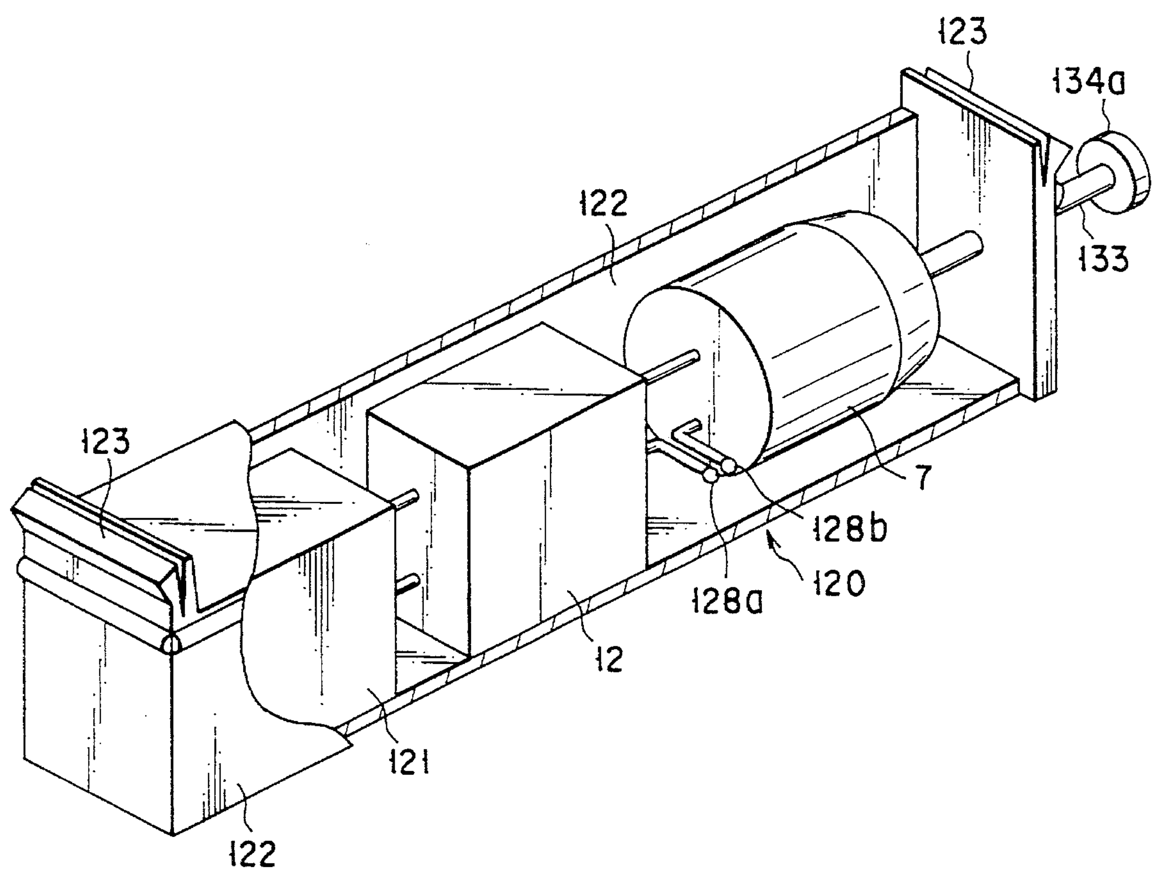
FIG. 23 is is a perspective view showing the internal structure of the electric unit shown in FIG. 22.

FIGS. 22 and 23 shows a tissue-fastening device according to a ninth embodiment of the invention. This device differs from the embodiments described above, in that it has a detachable electric unit. The insertion section (not shown) of the device may be the clipper 2A, the stapler 2B, the linear cutter 2C or the circular stapler 2D, as in the embodiments described above.

As shown in FIGS. 22 and 23, the operation section 1 contains a removable electric unit 120. The electric unit 120 comprises an electric motor 7, a control circuit 12 and a power supply 121. The motor 7 and the power supply 121 are, for example, a stepping motor and a lithium cell, respectively. The control circuit 12 controls the power from the power supply 121 to the electric motor 7.

The motor 7, the circuit 12 and the power supply 121 are covered by a protective box 122 which is made of a synthetic resin such as polysulfone or polyimide. Therefore, the electric unit 120 is a sealed component. The protective box 122 has integral legs 123, which are elastically fastened to the unit holder 126 of an electric-unit receptacle 125 located in the operation section 1.

The connection terminals for the motor 7 and the circuit 12 has contacts **128*a* and 128*b*, respectively. These contacts 128*a* and 128*b* oppose a contact plate 129. When pushed, the plate 129 will touch the contacts 128*a* and 128*b*. The contact plate 129 is formed integral with a push button 131. The push button 131 protrudes outwards through an opening made in the protective box 122. The protruding portion of the button 131 is covered by a watertight protective cover 132. The contacts 128*a* and 128*b*, the contact plate 129, the push button 131 and the cover 132 constitute a switch 130. The switch 130** is so positioned as to be operated by a surgeon who is manipulating the tissue-fastening device.

The shaft 133 of the motor 7 extends outwards from the rear side of the protective box 122 and is connected to a pinion shaft 137 by a coupling 134. The coupling 34 is composed of a coupling member **134*a* formed integral with the shaft 137 and a coupling member 134*b* formed with the pinion shaft 137. Mounted and fixed to the pinion shaft 137 is a first pinion 7*a*. The first pinion 7*a* is in mesh with a second pinion 7*b* which is mounted on a transmission shaft 13. Hence, the drive force of the electric motor 7 can be transmitted to the transmission shaft 13**.

The electric unit 120 can be removably set in a receptacle 125 which is a recess made in the casing 25 of the operation section 1. The opening of the receptacle 125 is closed by a cover 140.

It will be explained how the tissue-fastening device is operated to fasten body tissues.

when the electric unit 120 is set in the receptacle 125, the coupling 134 mechanically connects the shaft 133 of the motor 7 to the pinion shaft 137. When the surgeon pushes the button 131, the contact plate 129 electrically connects the contacts **128*a* and 128*b*, whereby the motor 7 is electrically connected to the control circuit 12. The circuit 12 supplies the power from the power supply 121 to the motor 7, driving the electric motor 7**.

The drive force of the motor 7 is transmitted to a drive shaft 15 by the worm gear **14*a* mounted on the transmission shaft 13 and the worm wheel 14*b* mounted on the drive shaft 15—in the same way as in the first embodiment shown in FIGS. 1 to 4. The pulleys 16*a* and 16*b*, both mounted on the drive shaft 15, are rotated, moving pusher links 17*a* and 17*b* back and forth through the casing 25 of the operation section 1. The pusher links 17*a* and 17*b* drive the insertion section (not shown) which is, for example, the clipper 2A**, in such a manner as has been explained before.

Thus does the electric unit 120 ultimately drive the clipper 2A. The clipper 2A applies clips to body tissues, thereby fastening the tissues together. Since the clipper 2A is electrically driven, the surgeon need not exert a relatively large force to operate the device and will not be tired so much as otherwise. For the same reason, the device has high operating efficiency. Even if the power supply 121 is used up while the tissue-fastening device, the operation section 1 can be continuously used, merely by replacing the power supply 121 with a new one. This helps to minimize the medical fees for fastening body tissues and also to abate problems relating to discarded medical materials.

Blood and washing solutions may wet the operation section 1 during the use of the tissue-fastening device. Nevertheless, they are prevented from entering the section 1 by a seal member 3*a* and an O-ring 4*a*. To wash and sterilize the operation section 1 after the use of the device, the clipper 2A is detached from the operation section 1 and a first connector 3 is sealed by a rubber cap. Then, blood, if any, is washed away from the operation section 1. The section 1 is sterilized. Once sterilized, the operation section 1 can be used again in combination of a new clipper 2A. This also serves to reduce medical fees.

The protective box 122 may be made of heat-resistant resin such as polysulfone or polyimide, pressure-resistant resin such as polyethylene, or vibration-resistant material such as vinyl chloride. Then, the box 122 can mitigate the adverse influence of heat, pressure, water or vibration on the the electric parts in the unit 120, i.e., the motor 7, the circuit 12 and the power supply 121, during the sterilization of the operation section 1.

Part of the protective box 122 may be made of electrically insulating material such as polyphenylene sulfide (PPS), stainless steel or ceramic. If the part of the box 122 is made of such a material, the possibility will be reduced that electric current or electric noise emanating from the electric parts of the unit 120 leaks outside the protective box 122.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A surgical device for applying surgical fasteners to body tissues in order to fasten the body tissues together, comprising:

an operation section having a housing having an inner space completely sealed from the outside;

drive means electrically driven and arranged in the inner space of said operation section;

an insertion section including a housing which has a first end portion containing the fasteners and having an opening through which the fasteners are to be applied, and a second end portion removably coupled to the housing of said operation section;

fastener-applying means located in the housing of said insertion section, for applying the fasteners from said opening to body tissues; and force-transmitting means for transmitting drive force from said drive means to said fastener-applying means.

2. The surgical device according to claim 1, wherein said force-transmitting means comprises at least one force-transmitting member having a first end portion extending and sealed from the housing of the operation section, and a second end portion coupled to said drive means to be driven by said drive means.

3. The surgical device according to claim 1, wherein said fastener-applying means has at least one bar-shaped member which is movable in the housing of said insertion section in the axial direction thereof.

4. The surgical device according to claim 3, wherein said fastener-applying means has means fixed in the vicinity of said opening of the housing of said insertion section, for abutting on a part of a fastener pushed by said at least one bar-shaped member and deforming the fastener.

5. The surgical device according to claim 3, wherein the housing of said insertion section contains a trap containing a plurality of surgical fasteners, and said at least one bar-shaped member pushes the fasteners from said trap one by one.

6. The surgical device according to claim 1, wherein said force-transmitting means comprises a plurality of force-transmitting members, each having a first end portion extending and sealed from the housing of the operation section, and a second end portion coupled to said drive means to be driven by said drive means.

7. The surgical device according to claim 1, wherein said fastener-applying means has at least two bar-shaped members which is movable independently of each other in the housing of said insertion section in the axial direction thereof.

8. The surgical device according to claim 7, wherein one of said at least two bar-shaped members pushes a surgical fastener from said opening, and another of said at least two bar-shaped members deforms the fastener pushed from said opening.

9. The surgical device according to claim 7, wherein said fastener-applying means has holding means located in the housing of said insertion section and near said opening, for temporarily holding the fastener pushed by said one of said at least two bar-shaped members, another of said at least two rod-shaped members is movable with respect to the holding means and deforming the fastener held by said holding means, and said operation section has force-transmitting means for transmitting a drive force from said drive means to said another of said at least two rod-shaped members.

10. The surgical device according to claim 7, wherein the housing of said insertion section contains a trap containing a plurality of surgical fasteners, and a first of said at least two bar-shaped member pushes the fasteners from said trap one by one.

11. The surgical device according to claim 1, further comprising an electric energy supplying unit located in the inner space of the housing of the operation section.

12. The surgical device according to claim 1, further comprising control means for supplying electric energy to said drive means from an electric energy supplying unit.

13. The surgical device according to claim 1, further comprising an electric energy supplying unit removably connected to the housing of the operation section.

14. The surgical device according to claim 1, further comprising an electric energy supplying unit located in the housing of the insertion section.

15. The surgical device according to claim 1, further comprising motion-converting means having discs rotated by said drive means and connecting rods for converting rotation of the discs to reciprocating motion and transmitting the reciprocating motion to said force-transmitting means.

16. A surgical device containing at least one surgical fastener and designed to apply the faster to body tissues in order to fasten the body tissues together, said device comprising:

an operation section having a housing having an inner space completely sealed from the outside;

drive means electrically driven and arranged in the inner space of said operation section;

an insertion section extending from said housing and including a distal end portion having an opening through which the fasteners are to be applied;

fastener-applying means located in said housing, for applying said at least one fastener from said opening to body tissues; and force-transmitting means for transmitting drive force from said drive means to said fastener-applying means.

17. The surgical device according to claim 16, further comprising a plurality of fastener-applying means for applying surgical fasteners of different types, one of which is selected and used.

18. The surgical device according to claim 16, wherein said force-transmitting means has adjusting means for adjusting at least one of physical quantities and is capable of transmitting a force to said fastener-applying means via said adjusting means, said physical quantities being a stroke and a force.

19. The surgical device according to claim 16, wherein said force-transmitting means comprises at least one force-transmitting member which has a first end portion extending from said housing in sealed condition and operatively coupled to said said drive means, and a second end portion operatively coupled to said fastener-applying means.

20. The surgical device according to claim 16, wherein said fastener-applying means has at least one bar-shaped member capable of moving in said insertion section in an axial direction thereof.

* * * * *